US007923242B2

(12) United States Patent
Kono et al.

(10) Patent No.: US 7,923,242 B2
(45) Date of Patent: Apr. 12, 2011

(54) MICROORGANISM DETECTION APPARATUS AND MICROORGANISM DETECTION CASSETTE

(75) Inventors: Eiji Kono, Gunma (JP); Hironobu Sekine, Gunma (JP); Yasuhiko Yokoi, Osaka (JP); Akihumi Iwama, Ibaraki (JP)

(73) Assignee: Sanyo Electric Co., Ltd., Osaka (JP)

( * ) Notice: Subject to any disclaimer, the term of this patent is extended or adjusted under 35 U.S.C. 154(b) by 1275 days.

(21) Appl. No.: 11/346,564

(22) Filed: Feb. 3, 2006

(65) Prior Publication Data

US 2006/0246578 A1 Nov. 2, 2006

(30) Foreign Application Priority Data

Feb. 3, 2005 (JP) .............................. 2005-027888
Jul. 13, 2005 (JP) .............................. 2005-204237

(51) Int. Cl.
*C12M 1/34* (2006.01)
*C12M 3/00* (2006.01)

(52) U.S. Cl. ............... 435/288.7; 435/286.2; 435/286.5; 435/287.2; 435/6

(58) Field of Classification Search ............... 435/288.7, 435/278.1–287.3, 286.5, 288.2, 287.1–287.2, 435/6, 286.1–286.6
See application file for complete search history.

(56) References Cited

U.S. PATENT DOCUMENTS

| 3,728,227 A * | 4/1973 | Elson et al. ................ 435/287.3 |
| 3,756,920 A | 9/1973 | Kelbaugh et al. |
| 4,576,916 A * | 3/1986 | Lowke et al. ............... 435/288.7 |
| 5,223,402 A * | 6/1993 | Abbas et al. ..................... 435/18 |
| 5,424,209 A * | 6/1995 | Kearney ...................... 435/286.5 |
| 5,648,232 A * | 7/1997 | Squirrell ......................... 435/34 |
| 6,096,272 A | 8/2000 | Clark et al. |
| 6,599,715 B1 * | 7/2003 | Vanderberg et al. ............ 435/34 |
| 2003/0040104 A1 * | 2/2003 | Barbera-Guillem ....... 435/286.2 |
| 2005/0237531 A1 * | 10/2005 | Roman .......................... 356/446 |

FOREIGN PATENT DOCUMENTS

| EP | 1 593 736 | 11/2005 |
| JP | 4-506149 | 10/1992 |
| JP | 9-98798 A | 4/1997 |
| JP | 2003-144194 A | 5/2003 |
| JP | 2004-229655 | 8/2004 |
| WO | WO 90/13639 | 11/1990 |
| WO | WO 2004/055203 A1 | 7/2004 |

* cited by examiner

*Primary Examiner* — Walter D Griffin
*Assistant Examiner* — Shanta G Doe
(74) *Attorney, Agent, or Firm* — McDermott Will & Emery LLP

(57) ABSTRACT

The objective of the present invention is to provide a simple microorganism detection apparatus that reduces detection time and that provides improved detection sensitivity, especially for gram-negative bacteria. The microorganism detection apparatus of the present invention includes: a detection target introduction portion, into which a sample and reagents are to be introduced; a detector, for detecting the color tone of the reagent introduced into the detection target introduction portion; a sample holder, for holding the sample to be introduced into the detection target introduction portion; a culture solution holder, for holding a culture solution used for microorganism culturing; and reagent holders, for holding the reagents to be introduced into the detection target introduction portion, wherein the presence/absence of microorganisms in the sample is determined based on the detected color tone.

14 Claims, 18 Drawing Sheets

MICROORGANISM DETECTION APPARATUS AND MICROORGANISM DETECTION CASSETTE

BACKGROUND OF THE INVENTION

The present invention relates to an apparatus for detecting microorganisms in a sample, and more specifically, relates to a microorganism detection apparatus and a microorganism detection cassette that are used in infectious disease diagnosis, bacteriological food examinations, environmental microorganism detection, or quality maintenance of washing water for semiconductors.

Recently, rapid advances have been made in technologies employed for the culturing and the provision of stem cells that, when introduced into the human body on the surface of medical instruments, reduce the possibility that the instruments will be violently rejected, and for the culturing of stem cells to obtain cells having specialized functions. For these cell culturing technologies, great care must be taken to ensure that the cells to be introduced into the human body are isolated and to prevent their contamination with microorganisms. Accordingly, accompanying advances in applicable systems engineering, there have been developed a number of microorganism detection methods, one of which employs a phenol oxidase precursor for this purpose (see, for example, Japanese Patent Laid-Open Publication No. Hei 09-098798).

Also available is a microorganism detection apparatus, disclosed in Japanese Patent Laid-Open Publication No. 2003-144194, that employs a sampling filter on which specific microorganisms are cultured for which fluorescence observation detection is performed.

However, when the conventional method that employs a phenol oxidase precursor is used, the sensitivity with which microorganisms, especially gram-negative bacteria, are detected is low. Further, when fluorescent observation is used for detection, although it is possible to measure specific microorganisms, light emitted by impurities can produce erroneous results.

SUMMARY OF THE INVENTION

While taking these problems into account, the objective of the present invention is to provide a simple microorganism detection apparatus, or a simple microorganism detection cassette, that shortens the time required for detection, and supplies improved detection sensitivity, especially for the detection of gram-negative bacteria.

According to a first aspect of the present invention, a microorganism detection apparatus comprises:

a detection target introduction portion, into which a sample and reagents are to be introduced;

a detector, for detecting optical characteristics of the reagent introduced into the detection target introduction portion;

a sample holder, for holding the sample to be introduced into the detection target introduction portion;

a culture solution holder, for holding a culture solution used to culture a microorganism; and reagent holders, for holding the reagent to be introduced into the detection target introduction portion, wherein the presence/absence of microorganisms in the sample is determined in accordance with optical characteristics detected by the detector.

According to a second aspect of the present invention, in the microorganism detection apparatus of the first aspect, the detector detects a color tone or absorbance of the reagent, and the presence/absence of microorganisms in the sample is determined in accordance with the color tone or the absorbance of the reagent detected by the detector.

According to a third aspect of the present invention, for the microorganism detection apparatus of the first or the second aspect, the culture solution is introduced into the detection target introduction portion and is used to culture the microorganisms in the detection target introduction portion.

According to a fourth aspect of the present invention, the microorganism detection apparatus of one of the first to the third aspects further comprises:

a temperature controller, located near the detection target introduction portion, for controlling temperature at the detection target introduction portion.

According to a fifth aspect of the present invention, for the microorganism detection apparatus of one of the first to the fourth aspects, the sample holder, the culture solution holder and the reagent holder are integrally formed, and a holder mounting unit is provided that is detachable from said microorganism detection apparatus.

According to a sixth aspect of the present invention, the microorganism detection apparatus of the fifth aspect further comprises:

a waste liquid collection portion, provided for the holder mounting unit, for collecting waste liquid for the sample, the culture solution or the reagent discharged from the detection target introduction portion.

According to a seventh aspect of the present invention, the microorganism detection apparatus according to the third or the fourth aspect further comprises:

a pressurizing unit, for pressurizing the sample holder, the culture solution holder and the reagent holder, wherein, using the pressurizing unit, the sample in the sample holder, the culture solution in the culture solution holder and the reagent in the reagent holder are fed directly to the detection target introduction portion.

According to an eighth aspect of the present invention, for the microorganism detection apparatus of the seventh aspect, each holder has adequate volume of each solution, through each pressurization process, the pressurizing unit feeds all the sample in the sample holder, all the culture solution in the culture solution holder and all the reagents in the reagent holders, respectively.

According to a ninth aspect of the present invention, for the microorganism detection apparatus of the seventh or the eighth aspect, the pressurizing unit includes a gas compression unit for supplying a compressed gas to the sample holder, the culture solution holder and the reagent holder.

According to a tenth aspect of the present invention, the microorganism detection apparatus of one of the seventh to the ninth aspects further comprises:

a plurality of sets of sample holders, culture solution holders, reagent holders, detection target introduction portions, and waste liquid collection portions, for collecting waste liquid for the sample, the culture solution or the reagent discharged from the detection target introduction portions.

According to an eleventh aspect of the present invention, for the microorganism detection apparatus of the tenth aspect, the optical characteristics of the reagent introduced into the plurality of detection target introduction portions are detected by employing a single detector.

According to a twelfth aspect of the present invention, for the microorganism detection apparatus of one of the ninth to the eleventh aspects, the culture solution holder, the reagent holder and the detection target introduction portion are mounted together in a single case that is tightly closed. Further, a communication portion, used to supply a compressed gas from the gas compression unit to the culture solution holder and the reagent holders, and a measurement portion, used by the detector to detect the optical characteristics of the reagent in the detection target introduction portion, are provided in the case.

According to a thirteenth aspect of the present invention, for the microorganism detection apparatus of the twelfth aspect, the sample holder is integrally formed in the case and a communication portion, used to supply a compressed gas from the gas compression unit to the sample holder, is provided in the case.

According to a fourteenth aspect of the present invention, for the microorganism detection apparatus of the twelfth aspect, the sample holder is connectable to the case.

According to a fifteenth aspect of the present invention, for the microorganism detection apparatus of one of the twelfth to the fourteenth aspects, the waste liquid collection portion, for collecting the waste liquid for the sample, the culture solution or the reagent discharged from the detection target introduction portion, is integrally formed with the case.

According to a sixteenth aspect of the present invention, for the microorganism detection apparatus of one of the twelfth to fourteenth aspects, the waste liquid collection portion, for collecting the waste liquid for the sample, the culture solution or the reagent discharged form the detection target introduction portion, is connectable to the case. According to the sixteenth aspect, in addition to the effects obtained by one of the twelfth to the fourteenth aspects, the waste liquid collection portion can be employed separately as a portion that should be exchanged each time used and as a portion that can be used without being exchanged.

According to a seventeenth aspect of the present invention, for the microorganism detection apparatus of one of the twelfth to the sixteenth aspects, the different case is provided for each detection target, and an identification unit for identifying the detection target in accordance with the case is provided.

A microorganism detection cassette according to an eighteenth aspect of the present invention is provided,
wherein a detection target introduction portion, into which a sample and reagents are to be introduced, a culture solution holder, for holding a culture solution to be introduced to the detection target introduction portion for culturing a microorganism, and reagent holders, for holding the reagents to be introduced to the detection target introduction portion, are mounted together in a single case; and
wherein a communication portion, used to supply a compressed gas to the culture solution holder and the reagent holders, and a measurement portion, used to detect optical characteristics of the reagent in the detection target introduction portion, are provided for the case.

According to a nineteenth aspect of the present invention, for the microorganism detection cassette of the eighteenth aspect, a sample holder, for holding a sample to be introduced into the detection target introduction portion, is arranged with the case, and a communication portion, for supplying the compressed gas to the sample holder, is provided for the case.

According to a twentieth aspect of the present invention, for the microorganism detection cassette of the eighteenth aspect, the sample holder, for holding a sample to be introduced into the detection target introduction portion by the compressed gas, is connectable to the case. According to the twentieth aspect, in addition to the effects obtained by the eighteenth aspect, detection of microorganisms can be efficiently performed.

According to a twenty-first aspect of the present invention, for the microorganism detection cassette of one of the eighteenth to the twentieth aspects, the waste liquid collection portion, for collecting the waste liquid for the sample, the culture solution or the reagents discharged from the detection target introduction portion, is integrally formed with the case.

According to a twenty-second aspect of the present invention, for the microorganism detection cassette of one of the eighteenth to twentieth aspects, the waste liquid collection portion, for collecting the waste liquid for the sample, the culture solution or the reagent discharged form the detection target introduction portion, is connectable to the case. According to the twenty-second aspect, in addition to the effects obtained by one of the eighteenth to the twentieth aspects, the waste liquid collection portion can be employed separately as a portion that should be exchanged each time used and as a portion that can be used without being exchanged.

According to the first aspect of the present invention, a microorganism detection apparatus comprises: a detection target introduction portion, into which a sample and reagents are to be introduced; a detector, for detecting optical characteristics of the reagent introduced into the detection target introduction portion; a sample holder, for holding the sample to be introduced into the detection target introduction portion; a culture solution holder, for holding a culture solution used to culture a microorganism; and reagent holders, for holding the reagents to be introduced into the detection target introduction portion, wherein the presence/absence of microorganisms in the sample is determined in accordance with optical characteristics detected by the detector. With a simple apparatus, the presence/absence of microorganisms in the sample can be determined.

According to the second aspect of the present invention, since the detector detects a color tone or absorbance of the reagent, the presence/absence of microorganisms in the sample can be easily determined in accordance with the color tone or the absorbance of the reagent detected by the detector.

According to the third aspect of the present invention, the culture solution is introduced into the detection target introduction portion and is used to culture the microorganisms in the detection target introduction portion. The detection time can be reduced, and the detection sensitivity can be increased.

According to the fourth aspect of the present invention, for the microorganism detection apparatus of one of the first to the third aspects, a temperature controller is located near the detection target introduction portion in order to control a temperature at the detection target introduction portion. Thus, the detection sensitivity can be further increased.

According to the fifth aspect of the present invention, for the microorganism detection apparatus of one of the first to the fourth aspects, the sample holder, the culture solution holder and the reagent holder are integrally formed, and a holder mounting unit is provided that is detachable from said microorganism detection apparatus. Therefore, the usability of the apparatus is improved.

According to the sixth aspect of the present invention, for the microorganism detection apparatus of the fifth aspect, a waste liquid collection portion is provided for the holder mounting unit to collect waste liquid for the sample, the culture solution or the reagent discharged from the detection target introduction portion. Thus, the apparatus can be produced more compactly.

According to the seventh aspect of the present invention, for the microorganism detection apparatus according to the third or the fourth aspect further comprises: a pressurizing unit, for pressurizing the sample holder, the culture solution holder and the reagent holders, wherein, using the pressurizing unit, the sample in the sample holder, the culture solution in the culture solution holder and the reagents in the reagent holders are fed directly to the detection target introduction portion. Thus, the sample in the sample holder, the culture solution in the culture solution holder and the reagents in the reagent holders can be easily introduced into the detection target introduction portion.

According to the eighth aspect of the present invention, for the microorganism detection apparatus of the seventh aspect, each holder has adequate volume of each solution, through each pressurization process, the pressurizing unit feeds all the sample in the sample holder, all the culture solution in the culture solution holder and all the reagents in the reagent holders, respectively. Thus, all the sample in the sample holder, all the culture solution in the culture solution holder and all the reagent in the reagent holder can be stably introduced into the detection target introduction portion.

According to the ninth aspect of the present invention, for the microorganism detection apparatus of the seventh or the eighth aspect, the pressurizing unit includes a gas compression unit for supplying a compressed gas to the sample holder, the culture solution holder and the reagent holders. Thus, the apparatus can be simplified.

According to the tenth aspect of the present invention, the microorganism detection apparatus of one of the seventh to the ninth aspects further comprises:

a plurality of sets of sample holders, culture solution holders, reagent holders, detection target introduction portions, and waste liquid collection portions, for collecting waste liquid for the sample, the culture solution or the reagent discharged from the detection target introduction portions. Therefore, a plurality of examinations can be performed at the same time, and the detection time can be reduced. Further, the presence/absence of microbial contamination can be precisely determined, and the detection sensitivity can be improved.

According to the eleventh aspect of the present invention, for the microorganism detection apparatus of the tenth aspect, the optical characteristics of the reagent introduced into the plurality of detection target introduction portions are detected by employing a single detector. The detection operation can be efficiently performed.

According to the twelfth aspect of the present invention, for the microorganism detection apparatus of one of the ninth to the eleventh aspects, the culture solution holder, the reagent holders and the detection target introduction portion are mounted together in a single case that is tightly closed. Further, a communication portion, used to supply a compressed gas from the gas compression unit to the culture solution holder and the reagent holders, and a measurement portion, used by the detector to detect the optical characteristics of the reagent in the detection target introduction portion, are provided in the case. Therefore, the microorganism detection apparatus can be protected from being contaminated by microorganisms.

According to the thirteenth aspect of the present invention, for the microorganism detection apparatus of the twelfth aspect, the sample holder is integrally formed in the case and a communication portion, used to supply a compressed gas from the gas compression unit to the sample holder, is provided in the case. The further contamination prevention effects can be expected.

According to the fourteenth aspect of the present invention, for the microorganism detection apparatus of the twelfth aspect, the sample holder is connectable to the case. Detection of microorganisms can be more efficiently performed.

According to the fifteenth aspect of the present invention, for the microorganism detection apparatus of one of the twelfth to the fourteenth aspects, the waste liquid collection portion, for collecting the waste liquid for the sample, the culture solution or the reagent discharged from the detection target introduction portion, is integrally formed with the case. The structure of the apparatus can be simplified.

According to the sixteenth aspect of the present invention, for the microorganism detection apparatus of one of the twelfth to fourteenth aspects, the waste liquid collection portion, for collecting the waste liquid for the sample, the culture solution or the reagent discharged form the detection target introduction portion, is connectable to the case. Therefore, the waste liquid collection portion can be employed separately as a portion that should be exchanged each time used and as a portion that can be used without being exchanged.

According to the seventeenth aspect of the present invention, for the microorganism detection apparatus of one of the twelfth to the sixteenth aspects, the different case is provided for each detection target, and an identification unit for identifying the detection target in accordance with the case is provided. The application for each case can be easily identified by the identification unit.

According to an eighteenth aspect of the present invention, a microorganism detection cassette is provided, wherein a detection target introduction portion, into which a sample and reagents are to be introduced, a culture solution holder, for holding a culture solution to be introduced to the detection target introduction portion for culturing a microorganism, and reagent holders, for holding the reagents to be introduced to the detection target introduction portion, are mounted together in a single case; and wherein a communication portion, used to supply a compressed gas to the culture solution holder and the reagent holder, and a measurement portion, used to detect optical characteristics of the reagent in the detection target introduction portion, are provided for the case. Therefore, detection of microorganisms can be efficiently performed.

According to the nineteenth aspect of the present invention, for the microorganism detection cassette of the eighteenth aspect, a sample holder, for holding a sample to be introduced into the detection target introduction portion, is arranged with the case, and a communication portion, for supplying the compressed gas to the sample holder, is provided for the case. Problems caused by microbial contamination can be prevented.

According to the twentieth aspect of the present invention, for the microorganism detection cassette of the eighteenth aspect, the sample holder, for holding a sample to be introduced into the detection target introduction portion by the compressed gas, is connectable to the case. Thus, detection of microorganisms can be efficiently performed.

According to the twenty-first aspect of the present invention, for the microorganism detection cassette of one of the eighteenth to the twentieth aspects, the waste liquid collection portion, for collecting the waste liquid for the sample, the culture solution or the reagent discharged from the detection target introduction portion, is integrally formed with the case. The structure of the apparatus can be simplified.

According to the twenty-second aspect of the present invention, for the microorganism detection cassette of one of the eighteenth to twentieth aspects, the waste liquid collection portion, for collecting the waste liquid for the sample, the culture solution or the reagent discharged form the detection target introduction portion, is connectable to the case. Therefore, the waste liquid collection portion can be employed separately as a portion that should be exchanged each time used and as a portion that can be used without being exchanged.

As described above, according to the microorganism detection apparatus and the microorganism detection cassette of the present invention, while the structure of the apparatus can be simplified, the detection time can be reduced and the detection sensitivity can be increased.

DETAILED DESCRIPTION OF THE PREFERRED EMBODIMENTS

A microorganism detection apparatus will now be described in detail in accordance with the preferred embodiments of the present invention, while referring to the accompanying drawings.

First Embodiment

Figure 1:
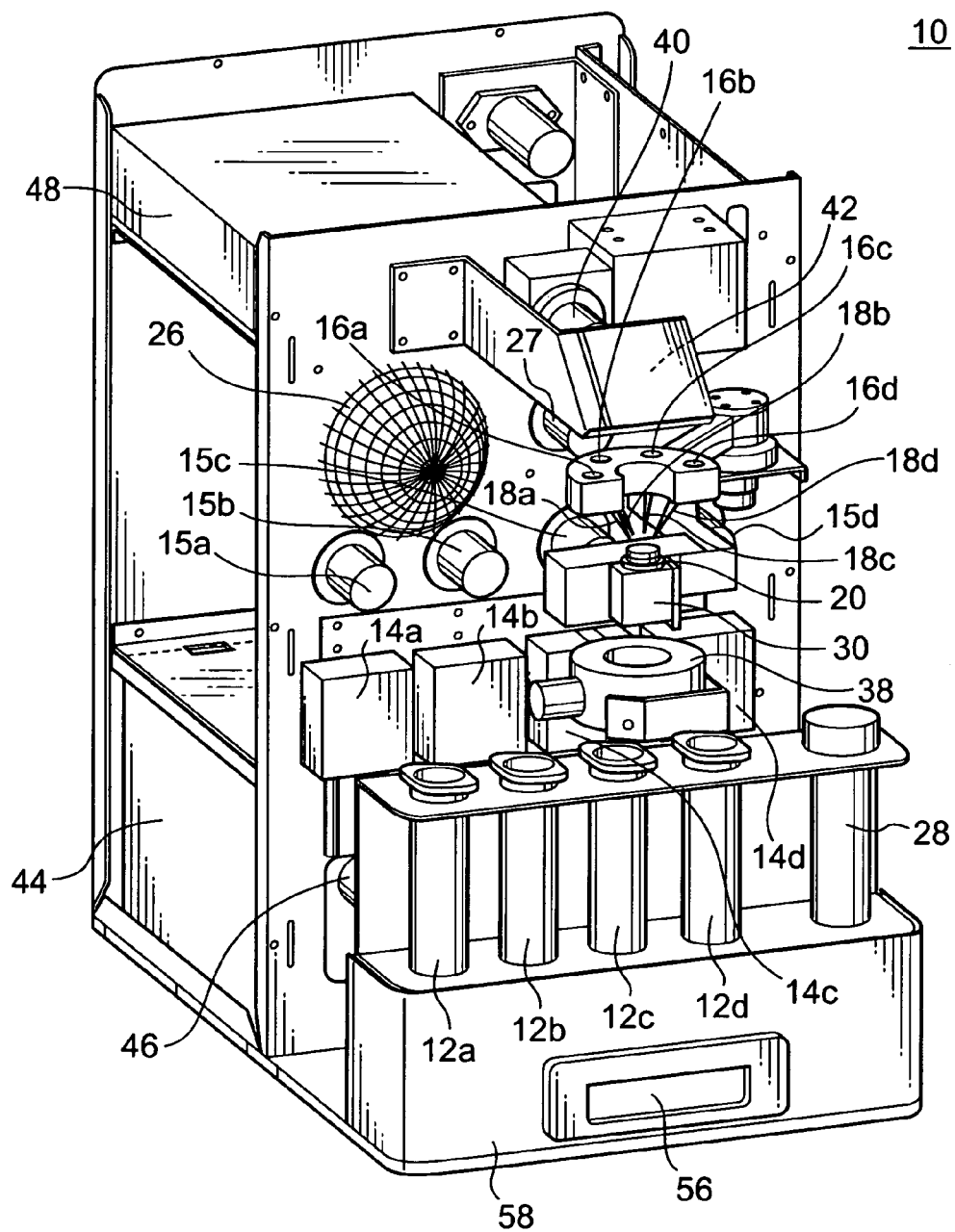
FIG. 1 is a perspective view of the internal structure of a microorganism detection apparatus according to a first embodiment of the present invention.
Figure 2:
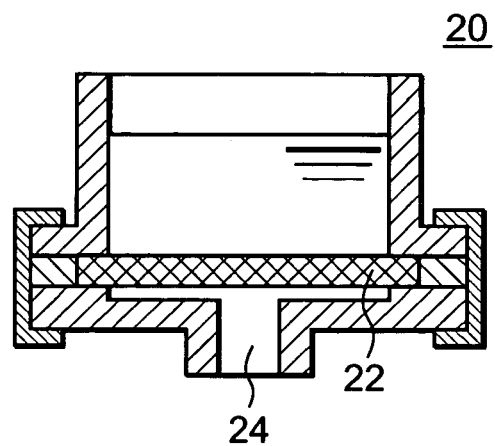
FIG. 2 is a schematic cross-sectional view of the internal structure of a detection target introduction portion.

FIG. 1 is a perspective view of the internal structure of a microorganism detection apparatus 10 according to the present invention. By using a pellster pump 14a, a sample to be detected is fed from a sample syringe (sample holder) 12a through a liquid line (not shown) to a sample injection port 16a. A pinch valve 15a is provided for a liquid feed line between the pelister gpump 14a and the sample injection port 16a, and is used to start and stop the feeding of liquid. A sample injection needle 18a is attached to the distal end of the sample injection port 16a, and a sample, when fed, is introduced into the detection target introduction portion 20 through the sample injection needle 18a. As shown in FIG. 2, a filter 22 is provided at the bottom of the detection target introduction portion 20, wherein a sample, when introduced, is retained. The diameter of the holes in the filter 22 range from 0.1 to 10 μm, but preferably are about 0.2 μm, and in this system, Ultrafree-MC by Millipore Corp. is employed. An outlet 24 is formed below the filter 22. By employing a pelister pump 26, a sample that has passed through the filter 22 is discharged through the outlet 24 and transmitted to a liquid waste tank (a waste liquid collection portion) 28. In this case, a pinch valve 27 is also located along a liquid line extending from the outlet 24 to the pelister pump 26 and to the liquid waste tank 28.

When the discharge of a sample from the detection target introduction portion 20 has been completed, a culture solution (in this embodiment, a medium that contains casamino acid as a main component) is fed from a culture solution syringe (a culture solution holder) 12b to the detection target introduction portion 20. Using the pellster pump 26, the same route as that used for the sample is employed to feed the culture solution, i.e., from the culture solution syringe 12b to a culture solution injection port 16b, through a different liquid line (not shown) from that used for the sample. A pinch valve 15b is is also provided for this liquid line. From the culture solution injection port 16b, the culture solution passes through a culture solution injection needle 18b and then reaches the detection target introduction portion 20. At this time, the pellster pump 26 is halted and the pinch valve 27 is closed, so that most of the culture solution injected into the detection target introduction portion 20 is retained on the filter 22.

Figure 3:
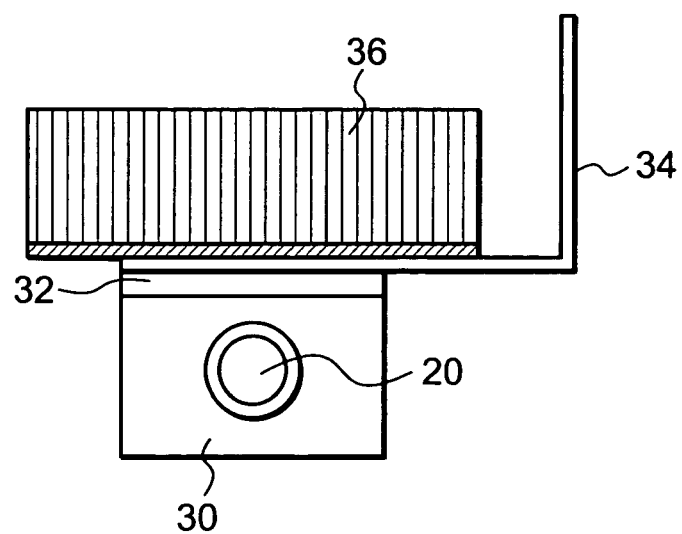
FIG. 3 is an enlarged schematic top view of the periphery of the detection target introduction portion.

The detection target introduction portion 20 is attached to and fitted in a heating block 30, and as shown in FIG. 3, a Peltier device (a temperature controller) 32 is provided for one side of the heating block 30. When a culture solution has been injected into the detection target introduction portion 20, the temperature in the detection target introduction portion 20 is adjusted to 35° C. to 40° C., preferably about 37° C. by the Peltier device 32 located near the detection target introduction portion 20. When microorganisms are present in the sample, the microorganisms are captured by the filter 22. When the culture solution is injected Into the detection target introduction portion 20, and is held at about 37° C. for several hours to half a day (nine hours in this embodiment), the microorganisms captured by the filter 22 increase, and as a result, one or several microorganisms that were captured are increased to $10^3$ or more. Thus, a number of microorganisms equal to or greater than the detection limit of a phenol oxidase precursor can be obtained. Further, a radiation plate 36 is arranged opposite the Peltier device 32 with an arm 34 positioned between them. When the temperature of the detection target introduction portion 20 is to be dropped after the culture process has been performed for nine hours at 37° C., the Peltier device 32 and the radiation plate 36 can be operated together to reduce the temperature within a short period of time. When culturing in the detection target introduction portion 20 is ended the pinch valve 27 is opened and the pelister pump 26 is activated to discharge the culture solution through the outlet 24 in the detection target introduction portion 20. The liquid line used for the discharge of the culture solution is the same as that used for the discharge of the sample. The discharged culture solution is transmitted to the liquid waste tank 28.

When the culture solution has been discharged from the detection target introduction portion 20, a pelister pump 14b feeds a washing reagent (water in this embodiment) from a washing reagent syringe 12c to the detection target introduction portion 20, along the same route as is used for the culture solution. The washing reagent is fed from the washing reagent syringe 12c to the washing reagent injection port 16c along a liquid line (not shown), for which a pinch valve 15c is provided differing from that used for the sample. The washing reagent is injected from the washing reagent injection port 16c, through a washing reagent injection needle 18c, into the detection target introduction portion 20. At this time, while the pelister pump 26 is being operated, the pinch valve 27 is open. The injected washing reagent cleans the detection target introduction portion 20 and is then discharged to the liquid waste tank 28 along the same liquid line as is used for the sample and the culture solution.

When the washing reagent has finally been discharged from the detection target introduction portion 20, a detection reagent (in this embodiment, an SLP reagent, a product of Wako Pure Chemical Industries Ltd.) is fed from a detection reagent syringe (a detection reagent holder) 12d to the detection target introduction portion 20, by a pelister pump 14d, along the same route as that used for the sample, the culture solution and the washing reagent. The detection reagent is fed from the detection reagent syringe 12d to a reagent injection port 16d through a liquid line (not shown), for which a pinch valve 15d is provided, differing from those used for the sample, the culture solution and the washing reagent. From the detection reagent injection port 16d, the detection reagent is injected, through a reagent injection needle 16d, into the detection target introduction portion 20. At this time, the pelister pump 26 is halted and the pinch valve 27 is closed, and the detection reagent injected into the detection target introduction portion 20 is retained on the filter 22 in the detection target introduction portion 20. Then, a ring light 38 is turned on, and a detector 40 detects a change in the color (at the filter 22) inside the detection target introduction portion 20.

The detector 40 detects the optical characteristics of the detection reagent introduced into the detection target introduction portion 20. Specifically, the detector detects either the color tone or the absorbance of the detection reagent in the detection target introduction portion 20, and in accordance with the color tone or the absorbance that is detected, also determines the presence/absence of microorganisms in the sample. The optical characteristics are the characteristics of a material, such as the color tone (a compound concept including saturation and brightness) or the absorbance of the material that can be detected optically. In this embodiment, a CCD camera 40 is employed as a detector, and employs the color tone of the detection reagent to determine the presence/absence of microorganisms in the sample.

Figure 4:
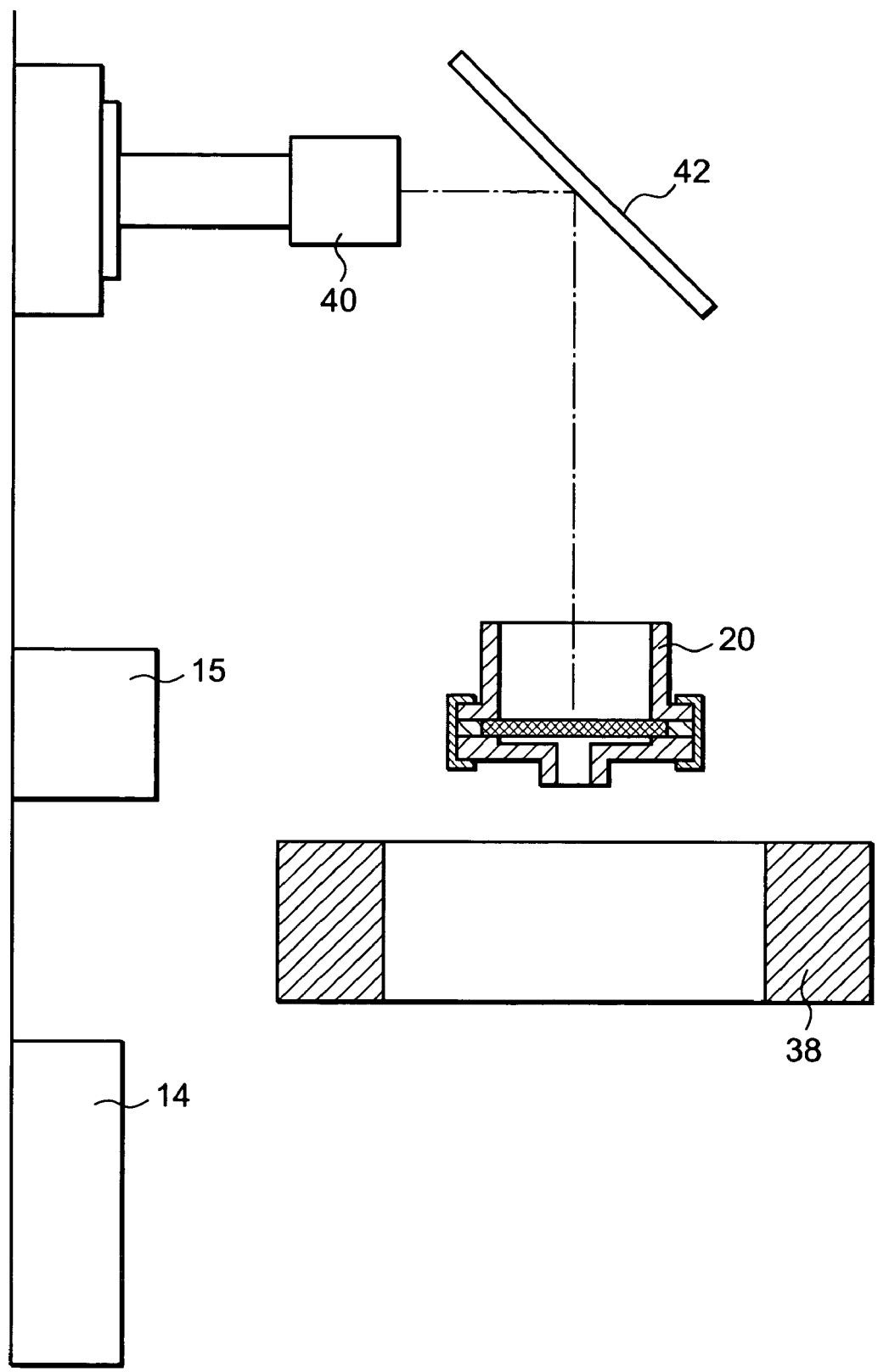
FIG. 4 is a schematic cross-sectional view of the positional relationship between a light source and a camera.

The ring light 38, the detection target introduction portion 20 and the CCD camera 40 are arranged as shown in FIG. 4. An image of the inside of the detection target introduction portion 20 exposed to the ring light 38 is refracted by a mirror 42 at an angle of 90°, and is obtained by the CCD camera 40. After the detection reagent has been introduced, photography is used to determine whether microorganisms are present. The ring light 38 is connected to a light source 44 by an optical fiber cable (not shown), and the light volume at the ring light 38 can be adjusted in advance using a control knob 46.

The starting and halting of the operation of the pelister pumps 14 and 26, the opening and closing of the pinch valves 15 and 27, the temperature control provided by the Peltier device 32, the turning on or off of the ring light 38, the photography for which the CCD camera 40 is used and the color tone change analysis made for an obtained image are performed by a controller 48. The control timing chart for the pelister pumps 14 and 26, the Peltier device 32 and the CCD camera 40 are shown in Table 1.

TABLE 1

Cleaning process timing chart example (Case of sample 100 ml and bacteria detection)

| | Sample filtering Process | | Cultivation Process | | Cleaing process | | Reagent reaction process | | | | | |
|---|---|---|---|---|---|---|---|---|---|---|---|---|
| | Sample injection | Negative-pressure open | Culture solution injection | Culturing | Washing reagent injection | Negative-pressure open | Reagent injection | 15 minutes later | 30 minutes later | 45 minutes later | 60 minutes later | Result determination | End |
| Operating time | one hour | Five seconds | Five seconds | Nine hours | Ten minutes | Five seconds | Five seconds | | | | | | |
| Sample pump (15a) | ON | OFF | OFF | OFF | OFF | OFF | OFF | | | | | | |

TABLE 1-continued

Cleaning process timing chart example (Case of sample 100 ml and bacteria detection)

| | Sample filtering Process | | Cultivation Process | | Cleaing process | | Reagent reaction process | | | | | | |
|---|---|---|---|---|---|---|---|---|---|---|---|---|---|
| | Sample injection | Negative-pressure open | Culture solution injection | Culturing | Washing reagent injection | Negative-pressure open | Reagent injection | 15 minutes later | 30 minutes later | 45 minutes later | 60 minutes later | Result determination | End |
| Culture solution pump (15b) | OFF | OFF | ON | OFF | OFF | OFF | OFF | | | | | | |
| Washing reagent pump (15c) | OFF | OFF | OFF | OFF | ON | OFF | OFF | | | | | | |
| Reagent pump (15d) | OFF | OFF | OFF | OFF | OFF | ON | ON | | | | | | |
| Waste liquid pump (26) | ON | OFF | OFF | OFF | ON | OFF | OFF | | | | | | |
| Negative-pressure open valve | Closed | Open | Closed | Closed | Closed | Open | Closed | | | | | | |
| Image fetching | | | | | | | | ON | ON | ON | ON | | |
| Temperature control | 25° C. | 25° C. | 37° C. | 37° C. | 25° C. | 30° C. | 30° C. | 30° C. | 30° C. | 30° C. | 30° C. | | |

The color tone change in the detection reagent used in this embodiment most easily occurs when a temperature of about 30° C. is maintained. Therefore, after the detection reagent has been injected, the temperature of the Peltier device 32 is adjusted so that the internal temperature of the detection target introduction portion 20 is 30° C. To maintain this temperature, a thermistor (not shown) is attached near the detection target introduction portion 20, on the heating block 30, to control the Peltier device 32 and ensure that the indicated thermistor temperature matches that shown in Table 1.

Figure 5:
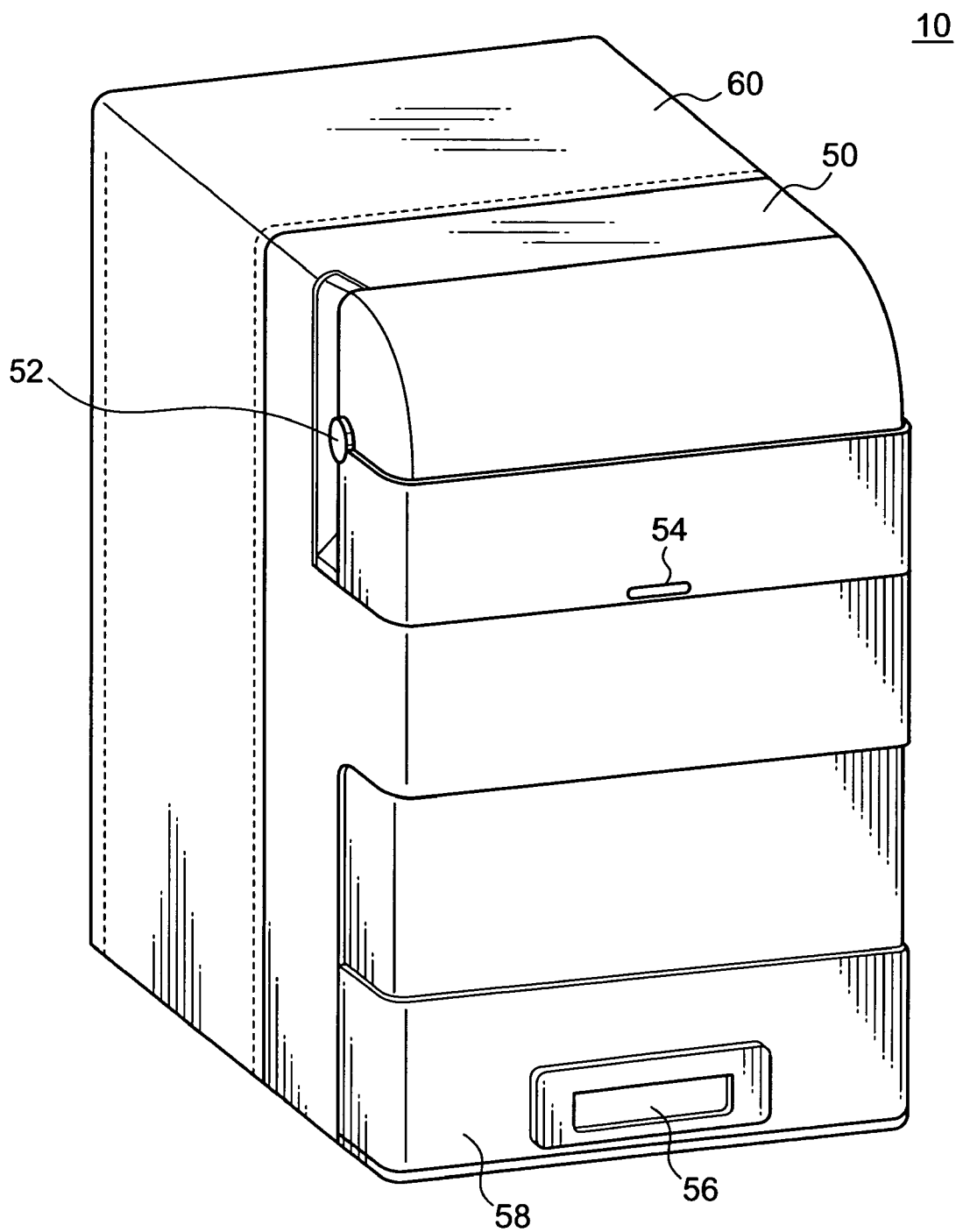
FIG. 5 is a diagram showing the external appearance of the microorganism detection apparatus.

FIG. 5 is a diagram showing the external appearance of the microorganism detection apparatus 10 with a lid 50 attached to the front face. An upper window 54, with a cover that pivots open and closed at a shaft 52, is formed in the upper portion of the lid 50. Through the upper window 54, the detection target introduction portion 20 can be observed or can be removed from the outside. In the lower portion of the lid 50 is a drawer 58 that can be drawn out using an attached handle 56. As shown in FIG. 1, the sample syringe 12a, the culture solution syringe 12b, the washing reagent syringe 12c, the detection reagent syringe 12d and the liquid waste tank 28 are arranged in the drawer 58. That is, these are integrally formed components of the drawer 58 and can be separated from the microorganism detection apparatus 10. Therefore, by exchanging drawers 58, samples, culture solutions, washing reagents, detection reagents and waste liquids can also be exchanged, all at the same time. Further, when the sample syringe 12a, the culture syringe 12b, the washing reagent syringe 12c, the detection reagent syringe 12d, the liquid feed lines, the sample injection port 16a, the culture solution injection port 16b, the washing reagent injection port 16c, the detection reagent injection port 16d, the sample injection needle 18a, the culture solution injection needle 18b, the washing reagent injection needle 18c, the detection reagent injection needle 18d, the detection target introduction portion 20 and the liquid waste tank 28 are integrally formed as a detachable package, the detection of microorganisms can be performed more efficiently.

The microorganism detection apparatus 10 of this embodiment can detect a variety of microorganisms. When, however, a specific microorganism is to be detected, or when there is only a rough idea of which microorganism is involved, it is preferable, during the culturing process, that instead of the temperature being set to 37° C., the temperature that is set should be one at which propagation of the microorganism occurs most naturally. For example, Eumycetes, such as *Candida Albicanis, Candida Lusitaniae, Candida Krusei, Candida Glabrata, Cryptococcus Neoformans, Aspergillus Fumigatus* and *Phenumocistis Carinii*, propagate most readily within a temperature range of around 30° C. Whereas for bacteria, such as *Bacillus Subtilis, Streptococcus Pyogenes, Salmonella Typhimurium, Salmonella Bongori, Salmonella Enteritidis, Escherichia Coli, Staphylococcus Epidermidis, Staphylococcus Aureus* and *Pseudomonas Aeruginosa*, the most favorable temperature range is around 37° C.

Since for the reagent used in this embodiment the detection sensitivity for gram-negative bacteria is lower than it is for the other Eumycetes and bacteria, after the culture solution is discharged the microorganism must be destroyed by drying or heating, or by employing ultrasound or a surfactant. Since peptidoglycan, which reacts with the detection reagent, is present inside the adventitia of a gram-negative bacterium, the detection sensitivity of the detection reagent is low. Thus, when the adventitia or the cytoplasmic film of the microorganism is destroyed by employing the above described method, peptidoglycan present between the adventitia and the cytoplasmic film of the gram-negative bacterium is exposed externally, and easily reacts with the detection reagent.

The detection reagent used in this embodiment reacts to the culture solution and changes in color tone in accordance with the components thereof. Therefore, the detection reagent was added to various types of culture solutions (culture solution components), and thereafter, the changes in color tones were observed. The observation results are shown in Table 2. The culture solution that did not react with the detection reagent is indicated by 0, and the culture solution that reacted with the detection reagent is indicated by x. The culture solution wherein, sixty minutes or longer after the detection reagent was added, a slight color tone change was identified at the visible level is indicated by Δ.

TABLE 2

| component | reactivity | Remarks |
|---|---|---|
| yeast extract | X | It is predicated that the enzyme will react with reagent A. |
| peptone | X | Peptone showed positive results, regardless of whether the protein was animal or vegetable. Since peptone performs an enzymolysis function for protein, it is predicated that, during this process, microorganisms will enter, or generated peptide will react with reagent A. |
| triptose | X | |
| triptonpeptone | X | |
| isotonpeptone | X | |
| caditone | X | |
| beef extract | Δ | Since enzymolysis did not occur, it is predicated that the entry of microorganisms was prevented, or a smaller amount of peptide was generated than was generated by peptone, so that a reaction with reagent A was difficult. |
| casamino acid | ○ | It is predicated that, since protein was hydrolyzed using acid, the entry of microorganisms was prevented, or it is predicated that since protein was decomposed to the level of amino acid, there was no reaction with reagent A. |
| L-arginine | ○ | Basically, amino acid did not react with reagent A. Thus, it is predicated that a reaction with reagent A will be obtained in a synthetic medium produced by mixing these amino acid components. |
| L-asparagine | ○ | |
| DL-potassium aspartate | ○ | |
| L-glutamine | ○ | |
| L-sodium glutamate | Δ | |
| L-histidine hydrochloride | ○ | |
| glycine | ○ | |
| L-cysteine | ○ | |
| ammonium chloride | ○ | The inorganic components, other than a nitrogen source used for the medium, did not react with reagent A. |
| glucose | ○ | |
| dipotassium hydrogenphosphate | ○ | |
| potassium dihydrogenphosphate | ○ | |
| magnesium sulfate | ○ | |
| ferrous sulfate | ○ | |
| sodium chloride | ○ | |

(reagent A: detection reagent)

As shown in Table 2, it is preferable that the medium used casamino acid as a natural component or a synthetic medium be employed as a culture solution when the detection reagent of this embodiment is employed. To use casamino acid is especially preferable when the costs and ease of culturing a microorganism are taken into account. Further, use of a meat extract is also available by adjusting the time following the addition of the detection reagent.

When a detection reagent other than those referred to in this embodiment is to be used, not only can casamino acid be employed, but also a glucose peptone liquid medium (GP liquid medium), a soy bean casein digest liquid medium (SCD liquid medium), a thioglycolic acid medium (TG medium), a Sabouroud glucose medium, a synthetic medium, brain heart infusion, Mueller-Hinton, common bouillon, or glucose peptone.

Several Eumycetes and bacteria examples have been enumerated. However, the microorganism detection system can also detect Eumycetes that belong, for example, to the genera *Candida, Hancenula, Saccharomyces, Tricosporon, Cryptococcus, Aspergillus, Penicillium, Blastomyces, Coccidioides, Pneumocistis, Malacesia* and *Dibothriomyces*, and bacteria that belong, for example, to the genera *Bacillus, Streptococcus, Pseudomonas, Escherichia, Staphylococcus, Lebusiera, Serratia, Shigella, Vibrio, Campylobacter, Clostridium* and *Erusinia*.

Second Embodiment

In the first embodiment, the pelister pumps have been employed to feed the sample, the culture solution, the washing reagent and the detection reagent, and the pinch valves have been employed to open and close the liquid feed lines. However, the pumps and valves are not limited to these, and components can be employed that include a function for feeding a required liquid from the individual holders to the detection target introduction portion, or from the detection target introduction portion to the waste liquid collection portion, and for halting the supply of the liquid. Therefore, air may be supplied to the individual holders by pelister pumps, and a sample, a culture solution, a washing reagent and a detection reagent may be fed by employing the pressure.

Figure 6:
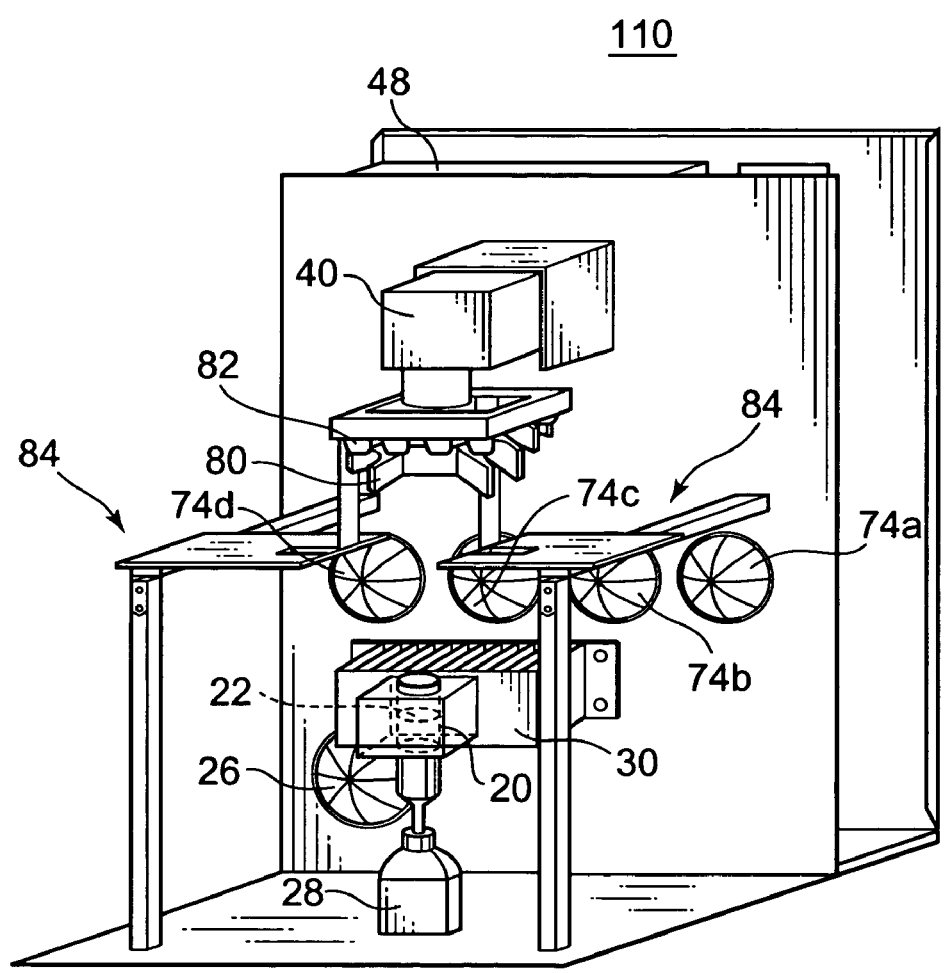
FIG. 6 is a perspective view of the internal structure of a microorganism detection apparatus according to a second embodiment of the present invention.
Figure 7:
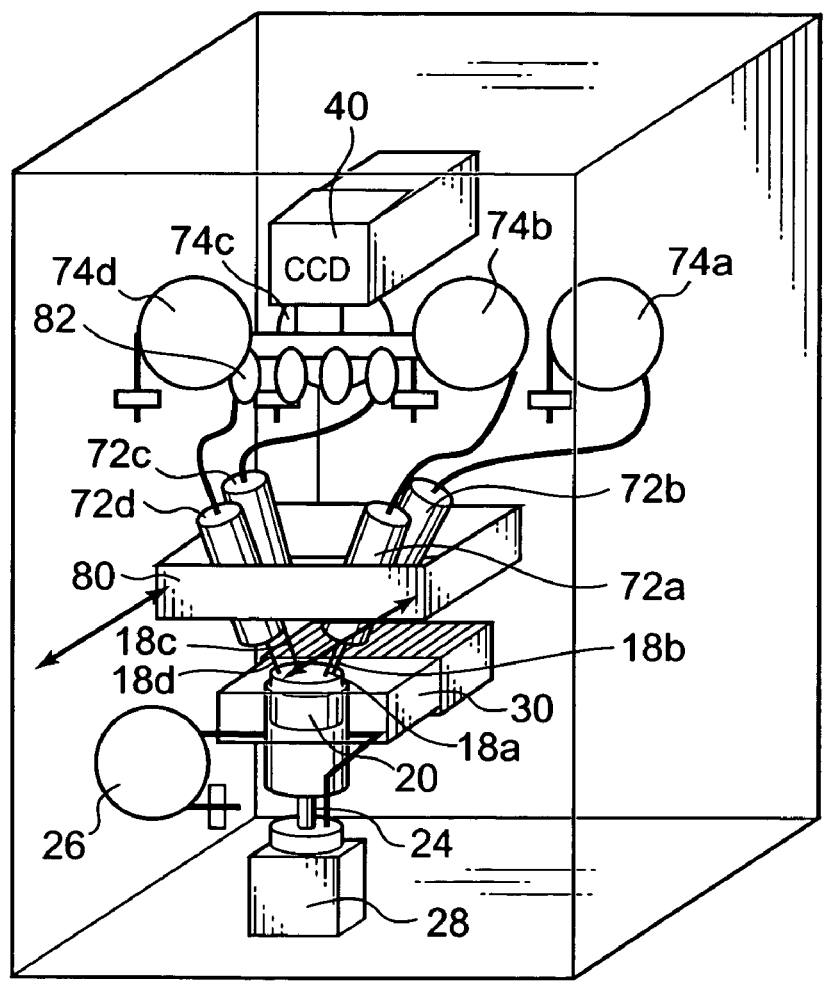
FIG. 7 is a schematic diagram showing the microorganism detection apparatus according to the second embodiment.

This case will be described in detail while referring to FIGS. 6 and 7. FIG. 6 is a perspective view of the internal structure of a microorganism detection apparatus 110 according to a second embodiment of the present invention. FIG. 7 is a schematic diagram showing the microorganism detection apparatus 110 in FIG. 6. The components in FIGS. 6 and 7 denoted by the same reference numerals as used in FIGS. 1 to 5 provide similar or the same effects as obtained in the first embodiment, and no further explanation for them will be given.

A holding unit 80 is provided that holds a sample syringe (sample holder) 72a, a culture solution syringe (culture solution holder) 72b, a washing reagent syringe 72c and a detection reagent syringe (reagent holders) 72d, and as indicated by arrows in FIG. 7, and is mounted so that it can be detached and removed from the microorganism detection apparatus 110 from the front and from the rear. That is, by exchanging the holding unit 80, the sample, the culture solution, the waste liquid and the detection reagent can be simultaneously replaced.

Lighting devices 82 in this embodiment are constituted by LEDs. The LED devices are positioned linearly to the front and to the rear of a CCD camera 40. A reinforcement member 84 is provided for the holding unit 80.

In this embodiment, pelister pumps 74a, 74b, 74c and 74d are pressure means for pressurizing the sample syringe (sample holder) 72a, the culture solution syringe (culture solution holder) 72b, the washing reagent syringe 72c and the detection reagent syringe (reagent holders) 72d, and for pressure feeding the sample, the culture solution, the washing reagent and the detection reagent in the syringes 72a, 72b, 72c and 72d directly to a detection target introduction portion 20.

Filters (not shown) are provided along the paths through which a compressed gas (air) is transmitted to the syringes 72a, 72b, 72c and 72d by the individual pelister pumps 74a, 74b, 74c and 74d. In the filters, as in the filters in the first embodiment, a plurality of pores are formed that have diameters of 0.1 to 1.0 μm or, preferably, about 0.2 μm.

Since, the pelister pumps 74a, 74b, 74c and 74d compress air that is then passed through the individual filters, before being transmitted to the syringes 72a, 72b, 72c and 72d, when germs are present in the air, the germs are captured by the filters. And thus, the possibility is avoided that the sample, the culture solution, the washing reagent and the detection reagent in the syringes 72a, 72b, 72c and 72d will be contaminated.

According to the pressurization method (pressure-feeding method), a gas (air) is employed that is compressed by the pelister pumps 74a, 74b, 74c and 74d and is used to impose pressure on the sample, the culture solution, the washing reagent and the detection reagent in the syringes 72a, 72b, 72c and 72d and to impel them directly to the detection target introduction portion 20. Therefore, unlike in the conventional case, and without having to depend on liquid lines, the sample, the culture solution, the washing reagent and the detection reagent in the syringes 72a, 72b, 72c and 72d can be forced out and fed to the detection target introduction portion 20. As a result, liquid feed lines are not required, and the number of parts can be reduced. Further, since an exchange of liquid feed lines is not required, the time required for the work period can be reduced.

Further, by employing a each pressure process, the each pelister pump 74a, 74b and 74d of this embodiment can impel, to the detection target introduction portion 20, all of the sample in the sample syringe 72a, all of the culture solution in the culture solution syringe 72b and all of the detection reagent in the reagent syringe 72d.

Thus, the volumes of a sample, a culture solution and a detection reagent that are to be used need only be stored in advance in the sample syringe 72a, the culture solution syringe 72b and the detection reagent syringe 72d, so that all the liquids in the individual syringes 72a, 72b and 72d can be expelled by a pressure produced by the pelister pumps 74a, 74b and 74d.

Since the apparatus is so designed that all the sample in the sample syringe 72a, all the culture solution in the culture solution syringe 72b and all the detection reagent in the detection reagent syringe 72d are forced out, by the application of a single pressure, complex and high-performance positive control is not required, and costs can be reduced.

An explanation will now be given for a microorganism detection method employing the microorganism detection apparatus 110 having the above described arrangement. For the microorganism detection apparatus 110, microorganism detection is enabled by employing the various reagents enumerated in the first embodiment and culture solutions that, for these reagents, are appropriate. In this embodiment, as in the first embodiment, an SLP reagent, by Wako Pure Chemical Industries Ltd., is employed, and a medium containing casamino acid as the primary element is employed as a culture solution.

Figure 8:
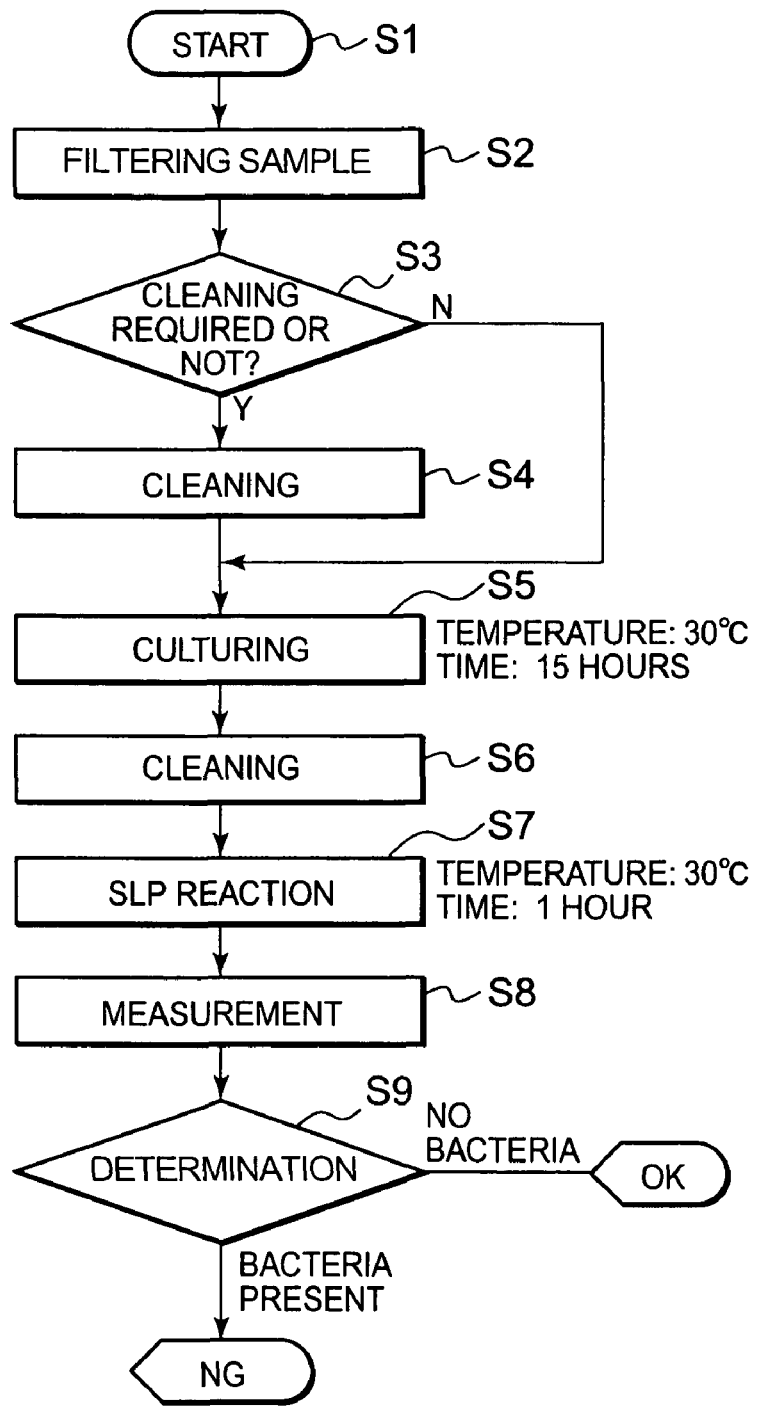
FIG. 8 is a flowchart showing the control process performed by the microorganism detection apparatus of the second embodiment.

In this embodiment, an explanation will be given for a microorganism detection method for a case wherein the microorganisms to be detected are not especially identified as being Eumycetes or bacteria. FIG. 8 is a flowchart showing the control processing performed by a controller 48 in this case. First, a predetermined volume of a sample is sealed in the sample syringe 72a as a detection target; a medium that contains a predetermined volume of casamino acid as the primary component is sealed in the culture solution syringe 72b; a washing reagent (water in this embodiment) is sealed in the washing reagent syringe 72c; and a predetermined volume of the SLP reagent is sealed in the detection reagent syringe 72d. These syringes 72a to 72d are arranged in the holding unit 80 that is then mounted to the microorganism detection apparatus 110. When the microorganism detection apparatus 110 is powered on, the controller 48 is activated (step S1 in FIG. 8).

When the controller 48 is activated at step S1 in FIG. 8, the controller 48 advances to a sample filtering process at step S2 in FIG. 8. In this process, the pelister pumps 74a and 26 are started by the controller 48. Then when the pelister pump 74a is started, external air is taken into the pelister pump 74a, and compressed. The compressed air is then supplied, through a filter (not shown), to the sample syringe 72a. With the compressed air, the interior of the sample syringe 72a is pressurized, and the sample to be detected is impelled out, through the sample injection needle 18a, to the detection target introduction portion 20. A filter 22 is provided for the detection target introduction portion 20, as in the first embodiment, and the impelled sample is retained in the detection target introduction portion 20. Further, an outlet 24 is formed below the filter 22, and through pressure applied by the pelister pump 26, the sample is passed through the filter 22 and discharged, through the outlet 24, to the liquid waste tank 28, which serves as a liquid waste collection portion. At this time, when microorganisms are present in the sample, the microorganisms are captured by the filter 22.

Thereafter, the discharge of the sample from the detection target introduction portion 20 is ended and the controller 48 advances to step S3 in FIG. 8. When cleaning of the controller 48 is required, the controller 48 advances to step S4, or when cleaning is not required, the controller 48 is shifted to step S5. Whether the cleaning should be performed following the filtering may be input to the controller 48 by a user, and in accordance with this input information, the controller 48 may determine, following the filtering, whether cleaning is required.

When it is determined at step S3 that cleaning is required, at step S4, the controller 48 activates the pelister pump 74c. When the pelister pumps 74c and 26 are started by the controller 48, a compressed gas is supplied by the pelister pump 72c, through a filter (not shown), to the washing reagent syringe 72c. As a result, the interior of the washing reagent syringe 72c is pressurized, and the washing reagent (water in this embodiment) is forced out through the washing reagent injection needle 18c and into the detection target introduction portion 20. The washing reagent is injected along the same route as is the sample, i.e., from the washing reagent syringe 72c through the washing reagent injection needle 18c to the detection target introduction portion 20. At this time, the washing reagent injected into the detection target introduction portion 20 is used to clean the detection target introduction portion 20, and thereafter is discharged through the same outlet 25, as is the sample, to the liquid waste tank 28.

Once the discharge of the washing reagent from the detection target introduction portion 20 has been ended, the controller 48 advances to the culturing process at step S5 in FIG. 8. At step S5, the controller 48 activates the pelister pump 74b, which then supplies a compressed gas through a filter (not shown) to the culture solution syringe 72b. Then, the interior of the culture solution syringe 72b is pressurized, and the culture solution (casamino acid in this embodiment) is injected, through the culture solution injection needle 18b, into the detection target introduction portion 20. At this time, most of the culture solution injected into the detection target introduction portion 20 is retained on the filter 22.

When the culture solution is injected into the detection target introduction portion 20, the controller 48 employs a Peltier device (not shown) to adjust the 30° C. temperature inside the detection target introduction portion 20. When this state is maintained for several hours to half a day (fifteen hours in this embodiment), the microorganisms captured by the filter 22 are increased from one to several at the captured time to $10^3$ or more. As a result, a microorganism count can be obtained that equals or exceeds the detection limit of the phenol oxidase precursor.

When the culturing in the detection target introduction portion 20 is ended, the controller 48 advances to the cleaning process at step S6 in FIG. 8. At step S6, the controller 48 activates the pelister pump 26 to discharge the culture solution through the outlet 24 of the detection target introduction portion 20, and activates the pelister pump 74c to supply a compressed gas to the washing reagent syringe 72c in the same manner as at step S4. As a result, the interior of the washing reagent syringe 72c is pressurized, and the washing reagent (water in this embodiment) is forced out, through the washing reagent injection needle 18c into the detection target introduction portion 20. The washing reagent injected into the detection target introduction portion 20 is used to clean the detection target introduction portion 20, and is discharged, thereafter, into the liquid waste tank 28.

When the discharge of the washing reagent from the detection target introduction portion 20 is ended, the controller 48 advances to the detection reagent reaction process at step S7. During this process, the controller 48 activates the pelister pump 74d to supply a compressed gas to the detection reagent syringe 72d. Then, the interior of the detection reagent syringe 72d is pressurized, and the reagent (in this embodiment, the SLP reagent by Wako Pure Chemical Industries Ltd.) is passed through the detection reagent injection needle 18d to the detection target introduction portion 20. At this time, the detection reagent injected into the detection target introduction portion 20 is retained on the filter 22 of the detection target introduction portion 20. Since the color tone change for the SLP reagent used in this embodiment occurs most easily when a temperature of about 30° C. is maintained, the controller 48 adjusts the temperature of the Peltier device so that the temperature inside the detection target introduction portion 20 is 30° C., and maintains this state for a predetermined period of time, e.g., one hour in this embodiment.

When one hour has elapsed, the controller 48 advances to a measurement process at step S8 in FIG. 8. During this process, the LED devices 82 are turned on, and the CCD camera 40 detects a change in the colors inside (filter 22) the detection target introduction portion 20. An image of the inside of the detection target introduction portion 20 is exposed by the LED devices 82 and is obtained by the CCD camera 40.

Thereafter, the controller 48 advances to a determination process at step S9 in FIG. 8. During this process, the presence/absence of microorganisms is determined by a color tone change analysis, performed by the filter 22, that is based on the image obtained by the CCD camera 40.

Third Embodiment

Figure 9:
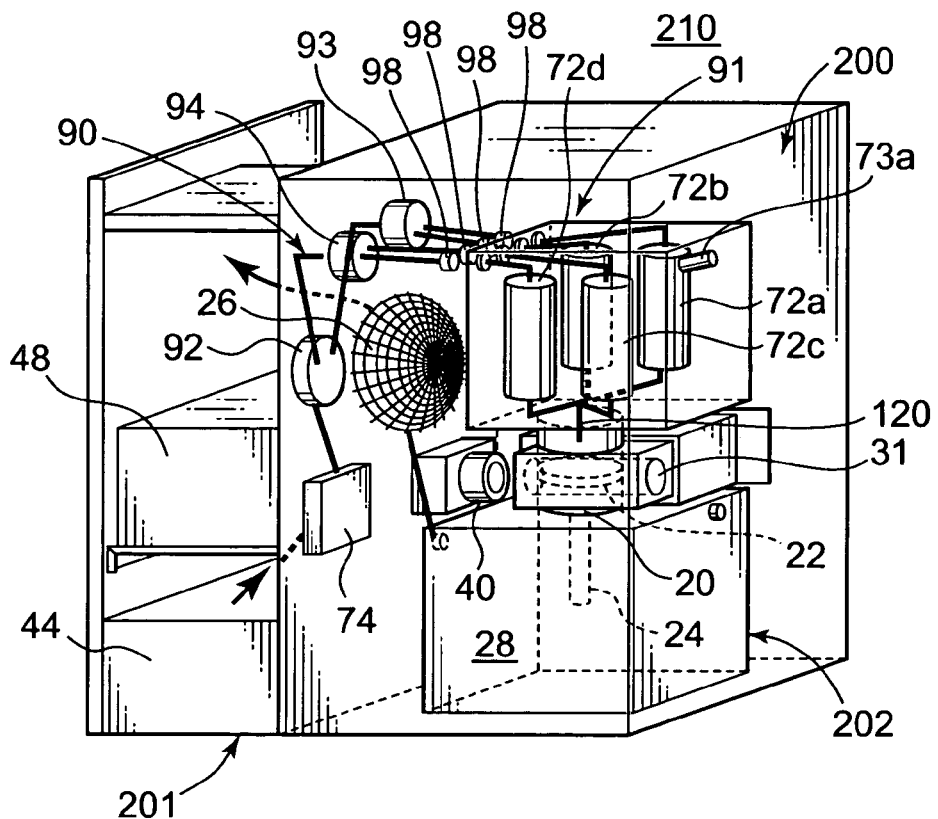
FIG. 9 is a perspective view of the internal structure of a microorganism detection apparatus according to a third embodiment of the present invention.

A microorganism detection apparatus equipped with a microorganism detection cassette will now be described in detail, in accordance with a third embodiment of the present invention, while referring to FIG. 9. FIG. 9 is a perspective view of the internal structure of a microorganism detection apparatus 210 according to this embodiment. In FIG. 9, components denoted by the same reference numerals as those used in FIGS. 1 to 8 provide similar or like effects, and no further explanation for them will be given.

Figure 10:
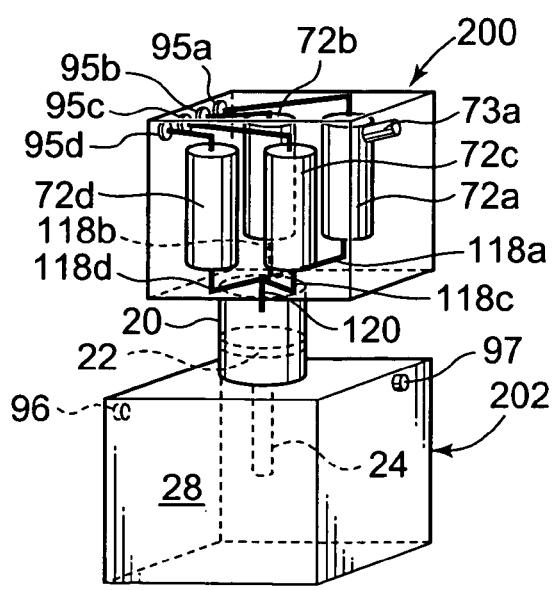
FIG. 10 is a perspective view of the internal structure of a microorganism detection cassette according to the third embodiment of the present invention.

The microorganism detection apparatus 210 in FIG. 9 comprises: a main body 201 and a microorganism detection cassette 200 provided so it can be detached and removed from the main body 201. As shown in FIG. 10, the microorganism detection cassette 200 includes: a detection target introduction portion 20, into which a sample and a reagent are to be introduced; a sample syringe (a sample holder) 72a, for holding a sample; a culture solution syringe (a culture solution holder) 72b, for holding a culture solution in which to culture microorganisms; a washing reagent syringe 72c, for holding a washing reagent to clean the detection target introduction portion 20; a detection reagent syringe (a detection reagent holder) 72d, for holding a reagent; and a liquid waste tank (a waste liquid collection portion) 28, in which waste liquid for the sample, the culture solution, the washing reagent or the detection reagent discharged from the detection target introduction portion 20 is to be collected. These components are mounted together in a single, tightly closed case 202.

The main body 201 includes: a controller 48, for controlling the microorganism detection apparatus 210; pelister pumps 74 and 26 that serve as pressure means; solenoid valves 92, 93 and 94, for controlling the supply of a compressed gas from the pelister pump 74 to the syringes 72a, 72b, 72c and 72d; a heating block 30, for heating the detection target introduction portion 20 to a predetermined temperature; and a CCD camera 40, which serves as a measurement unit (a detector) to detect the optical characteristics of the reagent in the detection target introduction portion 20. In this embodiment, since the CCD camera 40 is located to the side of the heating block 30, a through hole 31 that penetrates the heating block 30 horizontally (transversely) is formed in the heating block 30, so that the CCD camera 40 can detect the portion at the filter 22 in the detection target introduction portion 20.

The ends of airpipes 91, along which a compressed gas, supplied by the pelister pump 74 through an airpipe 90 in the main body 201, is introduced into the syringes 72a, 72b, 72c, 72c and 72d, communicate with upper ends of the individual syringes 72a, 72b, 72c and 72d of the microorganism detection cassette 200. The other ends of the air pipes 91 are connected to communication portions 95a, 95b, 95c and 95d, which are provided for the case 202. The communication portions 95a, 95b, 95c and 95d are used to detachably connect the airpipe 90 of the main body 201 and the airpipes 91 connected to the syringes 72a, 72b, 72c and 72d. When the airpipe 90 of the main body 201 and the airpipes 91 of the case 202 are connected by the communication portions 95a, 95b, 95c and 95d, the compressed gas from the pelister pump 74 can be supplied through the airpipes 90 and 91 to the syringes 72a, 72b, 72c and 72d.

A plurality (three in this embodiment) of solenoid valves 92, 93 and 94 are arranged along the airpipe 90 of the main body 201. The solenoid valves 92, 93 and 94 are three-way solenoid valves connected to the controller 48. In this embodiment, one pelister pump 74 is provided to supply a compressed gas to the syringes 72a, 72b, 72c and 72d, and the controller 48 adjusts the supply of the compressed gas, provided by the pelister pump 74, by controlling the solenoid valves 92, 93 and 94 provided along the airpipes 90 and 91.

Figure 11:
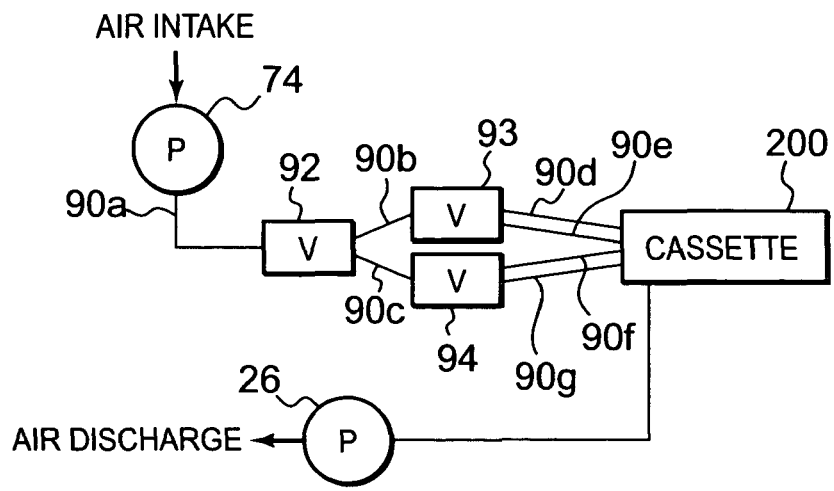
FIG. 11 is a diagram for explaining the compressed gas supply path for the microorganism detection apparatus of the third embodiment.

The path along which the compressed gas from the pelister pump 74 is supplied will now be described while referring to FIG. 11. When air (compressed gas) compressed by the pelister pump 74 is to be supplied to the sample syringe 72a, and the sample in the syringe 72a is to be introduced into the detection target introduction portion 20, the controller 48, in the main body 201, employs the solenoid valve 92 to connect to each other pipes 90a and 90b of the airpipe 90, and employs the solenoid valve 93 to connect pipes 90b and 90d.

Likewise, when a gas compressed by the pelister pump 74 is to be supplied to the culture solution syringe 72b, and the culture solution in the culture solution syringe 72b is to be introduced into the detection target introduction portion 20, the controller 48 employs the solenoid valve 92 in the main body 201 to connect the pipes 90a and 90b of the airpipe 90, and employs the solenoid valve 93 to connect pipes 90b and 90e.

Further, when a gas compressed by the pelister pump 74 is to be supplied to the washing reagent syringe 72c, and the washing reagent in the washing reagent syringe 74c is to be introduced into the detection target introduction portion 20, the controller 48 employs the solenoid valve 92, in the main body 201, to connect the pipes 90a and 90c of the airpipe 90, and employs the solenoid valve 94 to connect pipes 90c and 90f. Furthermore, when the gas compressed by the pelister pump 74 is to be supplied to the detection reagent syringe 72d, and the detection reagent in the detection reagent syringe 72d is to be introduced into the detection target introduction portion 20, the controller 48 employs the solenoid valve 92 to connect the pipes 90a and 90b of the airpipe 90 in the main body 2301, and employs the solenoid valve 94 to connect pipes 90c and 90g.

Filters 98 are provided along the airpipe 90 (the pipes 90d, 90e, 90f and 90g in this embodiment) of the main body 201, and a gas compressed by the pelister pump 74 is respectively supplied through the filters 98 to the syringes 72a, 72b, 72c and 72d. If by any chance germs should be present in the compressed gas supplied by the pelister pump 74, the germs can be captured by the filters 98, and the possibility that the sample, the culture solution, the washing reagent and the detection reagent will be contaminated can be avoided.

As described above, the microorganism detection cassette 200 is arranged inside a case 202. The interior of the case 202 communicates with the exterior via the communication portions 95a, 95b, 95c and 95d, which are connected to the airpipe 90 in the main body 201, a communication portion 96, to which a pipe is attached that connects the pelister pump 26 and the liquid waste tank 28, and a communication portion 97, which is used to control the pressure in the liquid waste tank 28. All of these communication portions are closed, for example, by plugs. As a result, a tightly closed space is defined inside the case 202, and contamination of the interior of the case 202 can be prevented.

On the other hand, the ends of liquid pipes 118a, 118b, 118c and 118d are connected to the lower ends of the syringes 72a, 72b, 72c and 72d, and the other ends are open at a liquid pipe 120 that communicates with the detection target introduction portion 20. The liquid pipes 118a, 118b, 118c and 118d are formed with a water-repellent finish in order to avoid leakage of the liquids from the syringes 72a, 72b, 72c and 72d. Therefore, during transportation, while liquids such as the reagents, are held in the syringes 72a, 72b, 72c and 72d, leakage of the liquids due to external vibrations or changes in the external temperature can be prevented. Pipes fitted with check valves may be employed as the liquid pipes 118a, 118b, 118c and 118d, and when a space is defined between the syringes 72a, 27b, 27c and 72d and the liquid pipes 118a, 118b, 118c and 118d, the leakage of individual liquids from the pipes 118a, 118b, 118c and 118d can be prevented.

While referring to the flowchart for the control process performed by the controller 48 in FIG. 8, an explanation will be given for a microorganism detection method that employs the microorganism detection apparatus 210 and the microorganism detection cassette 200 having the above described arrangement. In the microorganism detection cassette 200, a predetermined volume of a sample, for which a detection process is to be performed, is held in the sample syringe 72a, a predetermined volume of casamino acid is held in the culture solution syringe 72b, a washing reagent (washing water in this embodiment) is held in the washing reagent syringe 72c, and a predetermined volume of the SLP reagent is held in the detection reagent syringe 72d. First, the microorganism detection apparatus 210 is powered on and the controller 48 is activated (step S1 in FIG. 8).

When the controller 48 has been activated at step S1 in FIG. 8, the controller 48 advances to the sample filtering process at step S2 in FIG. 8. During this process, the controller 48 controls the individual solenoid valves 92, 93 and 94. That is, the controller 48 controls the solenoid valves 92, 93 and 94 so that the pipes 90a and 90b of the airpipe 90 can communicate with each other and so that the pipes 90b and 90d can communicate with each other to supply a gas compressed by the pelister pump 74 only to the reagent syringe 74a. Further, the controller 48 activates the pelister pumps 74 and 26. When the pelister pump 74 has been activated, external air is drawn in and is compressed, and the compressed air is supplied to the sample syringe 72a via the airpipe 90, the filter 98 and the airpipe 91. Then, the interior of the sample syringe 72 is pressurized, and the sample to be detected is fed through the sample pipe 118a and the liquid pipe 120 to the detection target introduction portion 20, and is retained therein.

When the pelister pump 26 is started, air in the liquid waste tank 28 is discharged by the pelister pump 26. Thus, the sample in the detection target introduction portion 20 passes through the filter 22, and travels, via the outlet 24, to the liquid waste tank 28. At this time, microorganisms present in the sample are captured in the filter 22.

When the discharging of the sample from the detection target introduction portion 20 is ended, the controller 48 advances to step S3 in FIG. 8. And then, when cleaning of the controller 48 is required, the controller 48 advances to step S4. When cleaning is not required, the controller 48 is shifted to step S5.

When it is determined at step S3 that cleaning is required, at step S4, the controller 48 controls the individual solenoid valves 92, 93 and 94, so that the pipes 90*a* and 90*c* of the airpipe 90 communicate with each other and so that the pipes 90*c* and 90*f* communicate with each other and supply a gas compressed by the pelister pump 74 only to the washing reagent syringe 74*c*. Further, the controller 48 activates the pelister pumps 74 and 26. And when the pelister pump 74 is started, external air is taken in and compressed, and the compressed gas is supplied to the washing reagent syringe 72*c* via the airpipe 90, the filter 98 and the airpipe 91. Then, the interior of the washing reagent syringe 72*c* is pressurized, and the washing reagent (washing water in this embodiment) is conveyed via the washing reagent pipe 118*c* and the liquid pipe 120 to the detection target introduction portion 20. At this time, the washing reagent, as it is injected, is used to clean the detection target introduction portion 20 and is then discharged via the same outlet 24 through which the sample was discharged to the liquid waste tank 28.

When the discharge of the washing reagent from the detection target introduction portion 20 has ended, the controller 48 advances to the culturing process at step S5 in FIG. 8. At step S5, the controller 48 controls the solenoid valves 92, 93 and 94, so that the pipes 90*a* and 90*b* of the airpipe 90 communicate with each other and are used to supply the gas compressed by the pelister pump 74 only to the culture solution syringe 74*b*. Further, the controller 48 activates the pelister pump 74, and when the pelister pump 74 is started, a gas is compressed and is supplied to the culture solution syringe 72*b* via the air pipe 90, the filter 98 and the airpipe 91. Then, the interior of the culture solution syringe 72*d* is pressurized, and the culture solution (casamino acid in this embodiment) is conveyed via the culture solution pipe 118*b* and the solution pipe 120 to the detection target introduction portion 20. At this time, most of the culture solution injected into the detection target introduction portion 20 is retained on the filter 22.

When the culture solution is injected into the detection target introduction portion 20, the controller 48 employs a Peltier device (not shown) to supply an adjusted temperature of 30° C. for the interior of the detection target introduction portion 20. When this state is maintained for several hours to half a day (fifteen hours in this embodiment), one to multiple microorganisms captured in the filter 22 are increased to $10^3$ or greater. As a result, a microorganism count equaling or exceeding the detection limit of the phenol oxidase precursor can be obtained.

When the culturing in the detection target introduction portion 20 has been ended, the controller 48 advances to the cleaning process at step S6 in FIG. 8. At step S6, the controller 48 starts the pelister pump 26 to discharge the culture solution through the outlet 24 of the detection target introduction portion 20. Furthermore, the controller 48 controls the solenoid valves 92, 93 and 94 and the pelister pump 74, so that the pipes 90a and 90c of the airpipe 90 communicate with each other and supply the gas compressed by the pelister pump 74 only to the washing reagent syringe 74c. As a result, the gas compressed by the pelister pump 74 is supplied to the washing reagent syringe 72c via the airpipe 90, the filter 98 and the airpipe 91, and the interior of the washing reagent syringe 72c is pressurized. Then, the washing reagent (washing water in this embodiment) is impelled via the washing reagent pipe 118c and the liquid pipe 120 to the detection target introduction portion 20. The washing reagent is injected into and is used to clean the detection target introduction portion 20, and is thereafter discharged to the liquid waste tank 28.

When the discharge of the washing reagent from the detection target introduction portion 20 is ended, the controller 48 advances to the reagent reaction process (the SLP reaction process) at step S7. At step S7, the controller 48 controls the solenoid valves 92, 93 and 94, so that the pipes 90a and 90c of the airpipe 90 communicate with each other and supply the gas compressed by the pelister pump 74 only to the reagent syringe 74d. Further, the controller 48 starts the pelister pump 74 to supply the gas thus compressed to the reagent syringe 74d. Then, the interior of the reagent syringe 72d is pressurized, and the reagent (in this embodiment, the SLP reagent by Wako Pure Chemical Industries Ltd.) is forced out, through the reagent pipe 118d and the liquid pipe 120, to the detection target introduction portion 20. At this time, the reagent injected into the detection target introduction portion 20 is retained on the filter 22. The color tone change of the SLP reagent used in this embodiment most frequently occurs when a temperature of about 30° C. is maintained. Thus, the controller 48 controls the temperature of the Peltier device to obtain a temperature of 30° C. for the interior of the detection target introduction portion 20, and maintains this state for a predetermined period of time, e.g., one hour in this embodiment.

When an hour has passed, the controller 48 advances to a measurement process at step S8 in FIG. 8 and turns on LED devices (not shown), and a CCD camera 40 detects a change of colors inside (filter 22) the detection target introduction portion 20. An image of the interior of the detection target introduction portion 20 illuminated by the LED devices is obtained by the CCD camera 40.

Thereafter, the controller 48 advances to a determination process at step S9 in FIG. 8, and determines the presence/absence of microorganisms through color tone change analysis of a portion of the filter 22, based on the image obtained by the CCD camera 40.

As described above, the syringes 72a, 72b, 72c and 72d, the detection target introduction portion 20 and the liquid waste tank 28 are mounted together in the closed case 202, and the entire package is provided as the microorganism detection cassette 200, which is detachable from the main body 201. Therefore, when the microorganism detection cassette 200 is simply mounted on the main body 201, while a sample, a culture solution, a washing reagent and a detection reagent are sealed in advance in the syringes 72a, 72b, 72c and 72d, the detection of microorganisms can be easily performed. According to this arrangement, the detection of microorganisms can be performed more efficiently, and the contamination occasioned by the entry of external germs can be prevented to the extent possible. Furthermore, the filter 22 in the detection target introduction portion 20 can be protected from drying out during the detection process.

Furthermore, since the microorganism detection cassette 200 is a closed type, the cassette 200 can also be employed for the detection of anaerobic bacteria. Therefore, in general, usage of the microorganism detection apparatus 210 can be improved by employing the microorganism detection cassette 200.

Figure 12:
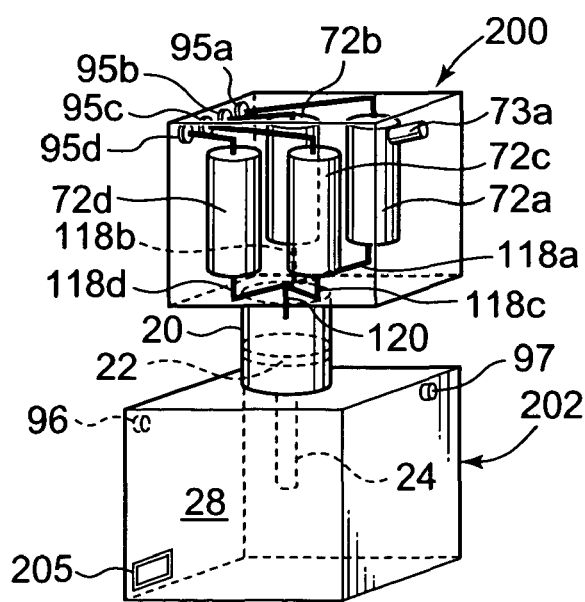
FIG. 12 is a perspective view of the internal structure of a microorganism detection cassette wherein an identification unit is attached to a case.

When the case 202 of the microorganism detection cassette 200 is separated in accordance with samples (detection targets), the applications to be employed for the individual cases can be easily identified. For example, cases having different shapes are used in consonance with samples, or as shown in FIG. 12, an identification portion 205 is formed in the case 202 to provide easy identification of the application in each case. As a result, an examination can be smoothly performed.

In addition, the identification portion 205 is formed, for example, of a barcode, and a reader for reading the barcode is provided for the main body 201. In this case, based on information input by the reader, the controller 48 can control the culturing period and the culturing temperature, and the detection operation can be performed more efficiently.

Fourth Embodiment

Figure 13:
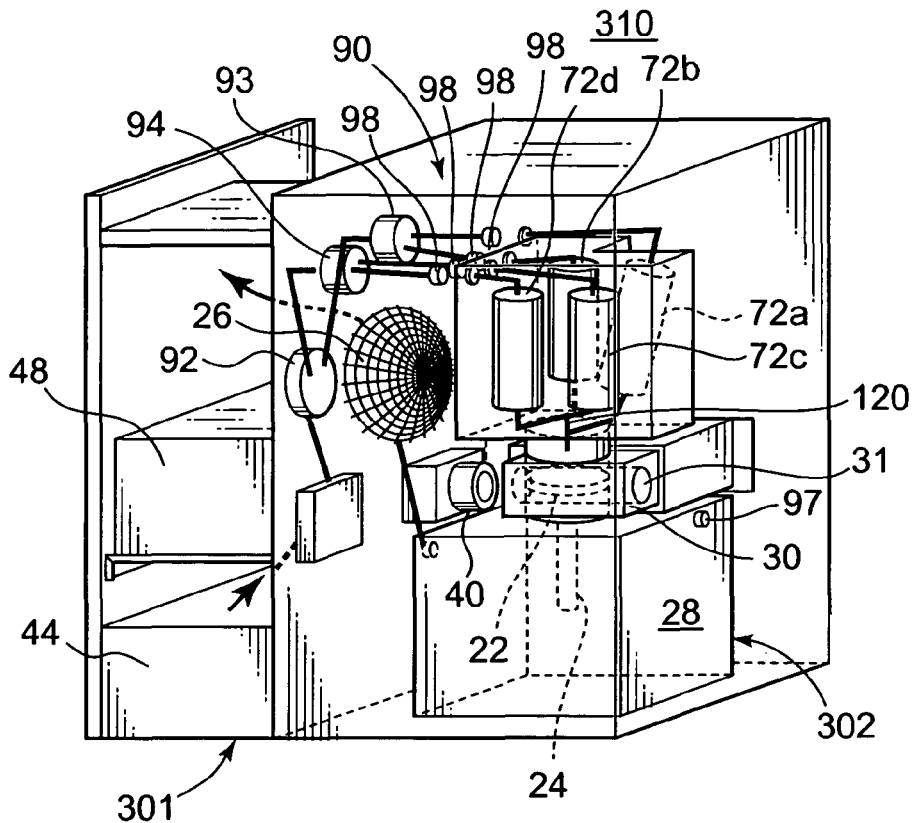
FIG. 13 is a perspective view of the internal structure of a microorganism detection apparatus according to a fourth embodiment of the present invention.
Figure 14:
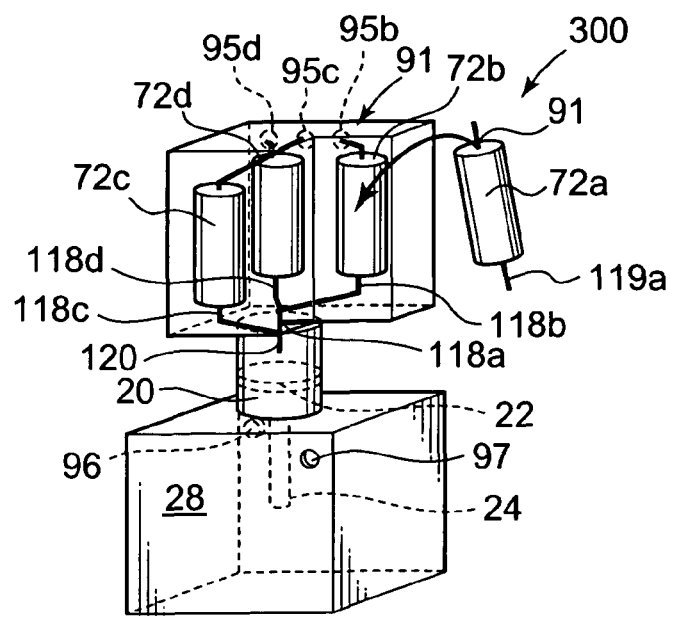
FIG. 14 is a perspective view of the internal structure of a microorganism detection cassette according to the fourth embodiment of the present invention.

In the third embodiment, for the microorganism detection cassette 200 of the microorganism detection apparatus 210, the sample syringe 72a has also been formed and included in the case 202. However, as shown in FIGS. 13 and 14, a sample syringe 72a may be so provided that it can be connected to a case 302. FIG. 13 is a perspective view of the internal structure of a microorganism detection apparatus 310 when the sample syringe 72a can be connected to the case 302. And FIG. 14 is a perspective view of the internal structure of a microorganism detection cassette 300. In FIGS. 13 and 14, components denoted by the same reference numerals as are used in FIGS. 1 to 12 provide similar or like effects.

In this case, a liquid pipe 118a provided for the case 302 can be closed, for example, by using a valve or a tight stopper. Likewise, a liquid pipe 119a connected to the lower end of the sample syringe 72a can, for example, be closed by using a valve or a tight stopper. Furthermore, the sample syringe 72a can be connected to the case 302 simply by connecting the liquid pipe 118a and the liquid pipe 119a. And the sample syringe 72a can be connected to a main body 301 simply by connecting an airpipe 90, at the upper end of the sample syringe 72a, to an airpipe 91 in the main body 301.

When the sample syringe 72a and the case 302 can be connected, individual liquids are introduced, in advance, into a culture solution syringe 72b, a washing reagent syringe 72c and a reagent syringe 72d can be mounted together in the case 302, a microorganism detection cassette 300 that includes such a case 302 can be prepared, and communication portions 95b, 95c, 95d, 96 and 97 and the liquid pipe 118a can be closed. Then, contamination of the case 302 by a variety of germs can be prevented. Furthermore, immediately before the detection process is started, the sample can be sealed inside the sample syringe 72a, which is then attached to the case 302. In this manner, the microorganism detection cassette 300 can easily be assembled. And therefore, by employing the microorganism detection cassette 300 of this embodiment, the detection of microorganisms can more efficiently be performed.

Fifth Embodiment

Figure 15:
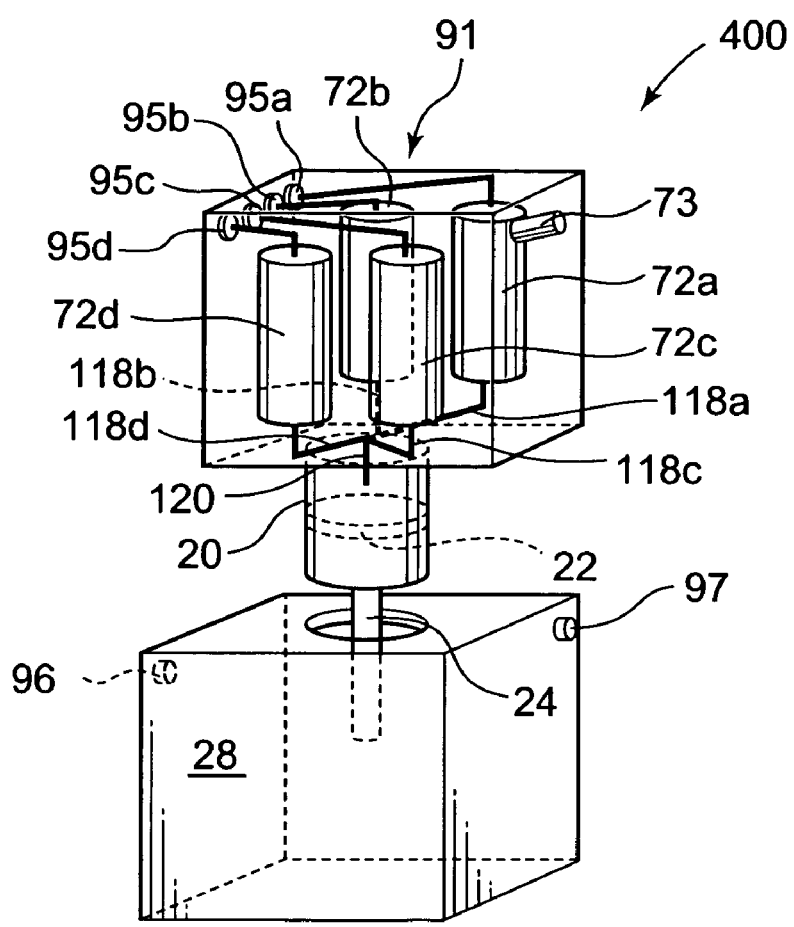
FIG. 15 is a perspective view of the internal structure of a microorganism detection cassette according to a fifth embodiment of the present invention.

In the third and fourth embodiments, the liquid waste tank 28 is integrally formed in the case 202 or 302. However, a liquid waste tank may be one that can be connected to a case. FIG. 15 is a perspective view, in such a case, of the internal structure of a microorganism detection cassette 400 and a liquid waste tank 28. In FIG. 15, the components denoted by the same reference numerals as used in FIGS. 1 to 14 provide similar or like effects, and no further explanation for them will be given.

In this embodiment, since the liquid waste tank 28 is connected to a case 402, repetitive reuse of the liquid waste tank 28 is possible. That is, individual syringes 72a, 72b, 72c and 72d and a detection target introduction portion 20 must be exchanged following every microorganism detection process, while the liquid waste tank 28 need not be exchanged so often. Therefore, since those portions that can be used only once are integrally formed with the case 402, and a reusable liquid waste tank 28 is provided that can be connected to the case 402 but need not be replaced following each procedure, the costs can be reduced.

Sixth Embodiment

Figure 16:
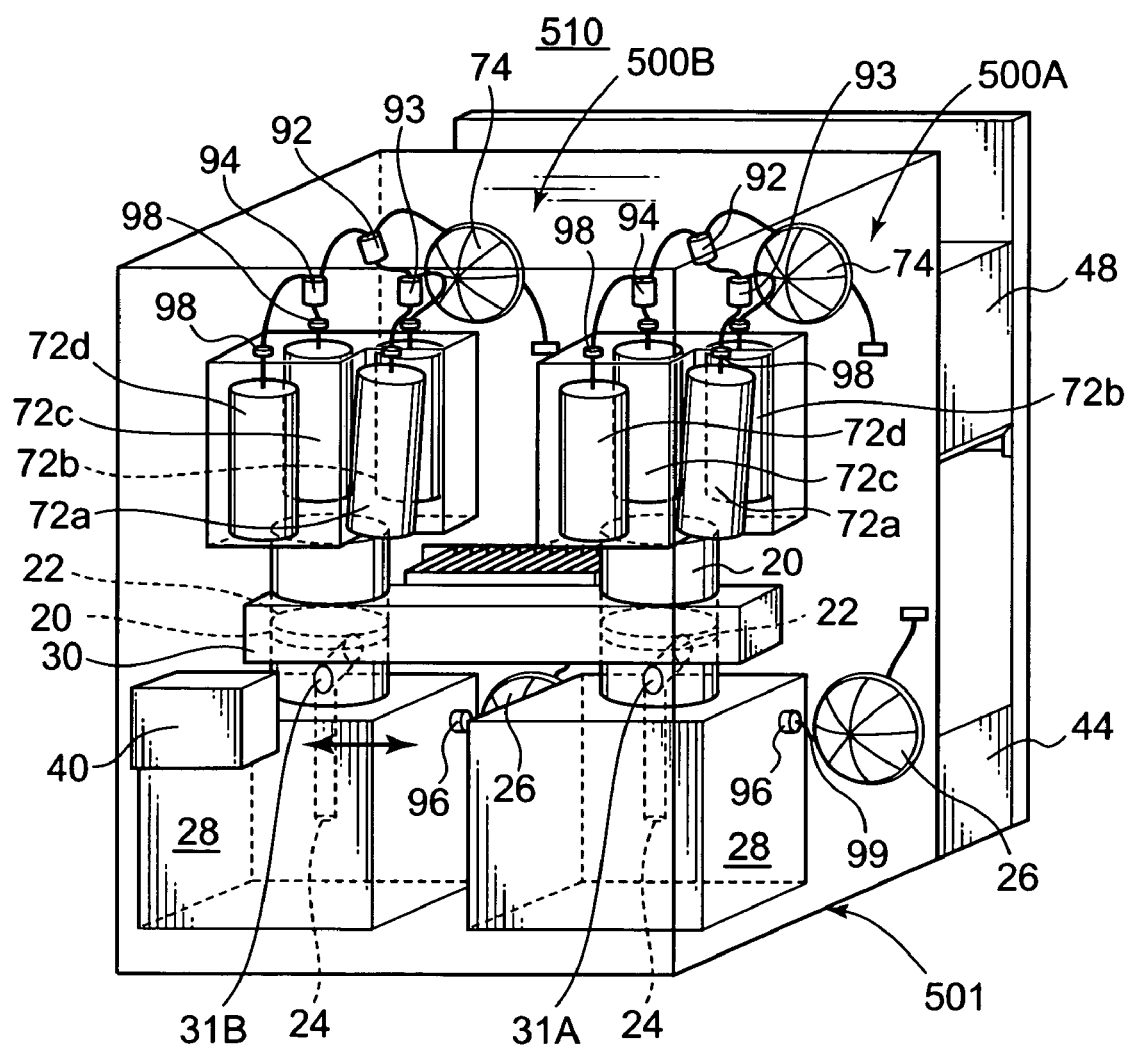
FIG. 16 is a perspective view of the internal structure of a microorganism detection apparatus according to a sixth embodiment of the present invention.

For the microorganism detection apparatus of the third to the fifth embodiments, one microorganism detection cassette is detachably mounted on the main body. Further, as shown in FIG. 16, two microorganism detection cassettes 500A and 500B can also be connected to a main body 501. FIG. 16 is a perspective view of the internal structure of a microorganism detection apparatus 510 that includes two microorganism detection cassettes 500A and 500B. In FIG. 16, components denoted by the same reference numerals as those used in FIGS. 1 to 15 provide similar or like effects, and no further explanation for them will be given.

As shown in FIG. 16, a CCD camera 40 is provided on one side (the front in FIG. 16) of the main body 501, and is horizontally (transversely) movable in this embodiment. Through holes 31A and 31B that penetrate a heating block 30 horizontally (from the front to the rear in FIG. 16) are formed in the heating block 30, to hold detection target introduction portions 20 that are provided for the microorganism detection cassettes 500A and 500B, and portions of filters 22 for the detection target introduction portions 20 can be detected by the CCD camera 40.

Since the two microorganism detection cassettes 500A and 500B can be detached from the main body 501, two examinations can be performed at the same time. For example, a sample for which an examination for microbial contamination is to be performed can be sealed in a sample syringe 72a for the microorganism detection cassette 500A, while a sample that has already been contaminated by microorganisms can be sealed in a sample syringe 72a for the microorganism detection cassette 500B, and the examinations can be performed at one time. By comparing the results obtained, microbial contamination of the sample provided for the microorganism detection cassette 500A can be easily determined.

Likewise, a sample for which an examination for microbial contamination is to be performed can be sealed in the sample syringe 72a of the microorganism detection cassette 500A, while a sample that has not been contaminated by microorganisms can be sealed in the sample syringe 72a of the microorganism detection cassette 500B, and the examinations can be performed at one time. By comparing the obtained results, microbial contamination of the sample provided for the microorganism detection cassette 500A can be readily determined.

Since two examinations can be performed at one time, there is no difference in the parameters, such as temperature and humidity, for the samples that are to be examined, microbial contamination determinations can be precisely performed. Therefore, the detection sensitivity can be improved.

Seventh Embodiment

Figure 17:
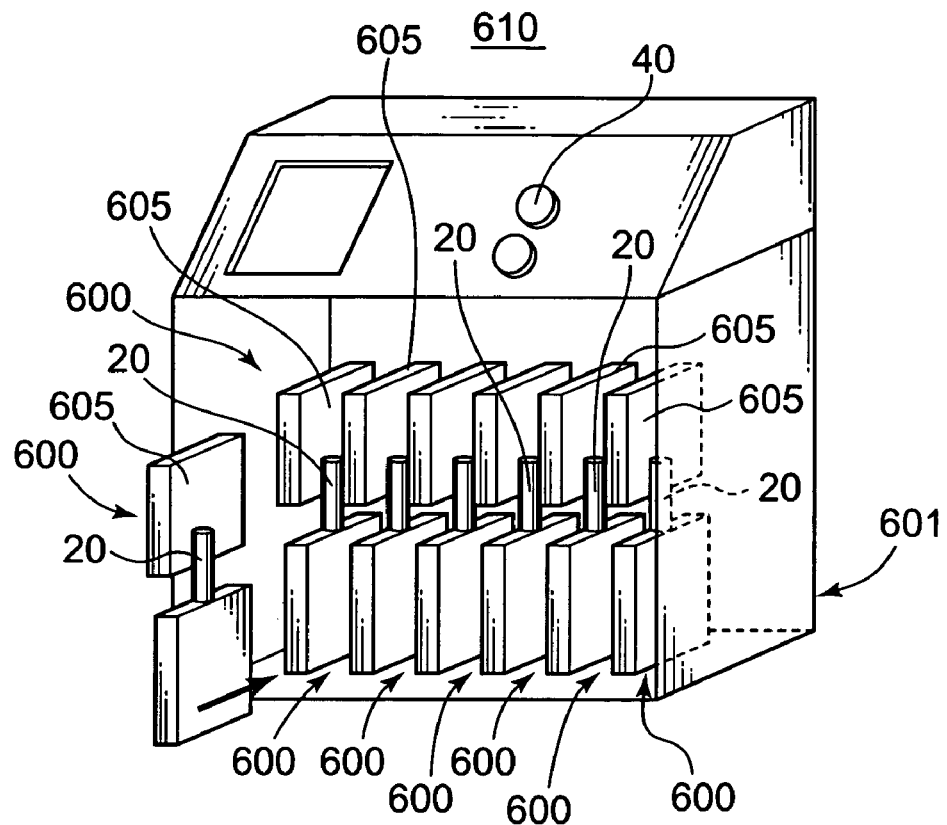
FIG. 17 is a perspective view of the internal structure of a microorganism detection apparatus according to a seventh embodiment of the present invention.

Not only can two microorganism detection cassettes be detachably provided for the main body, as in the sixth embodiment, but three or more microorganism detection cassettes can be so provided. FIG. 17 is a schematic perspective view of a microorganism detection apparatus 610, according to a seventh embodiment of the present invention, for which a plurality of microorganism detection cassettes 600 are provided.

As shown in FIG. 17, seven microorganism detection cassettes 600 are detachably provided for a main body 601 of the microorganism detection apparatus 610 of this embodiment. Sample syringes, culture solution syringes, washing reagent syringes and reagent syringes are stored in boxes 605, positioned above and to one side of detection target introduction portions 20, that serve as constituents of a case 602. The syringes communicate with the respective detection target introduction portions 20 via liquid pipes (not shown) connected to the lower ends of the individual syringes. Since no components are located immediately above the detection target introduction portions 20, filters inside the detection target introduction portions 20 can be examined from immediately above.

Figure 18:
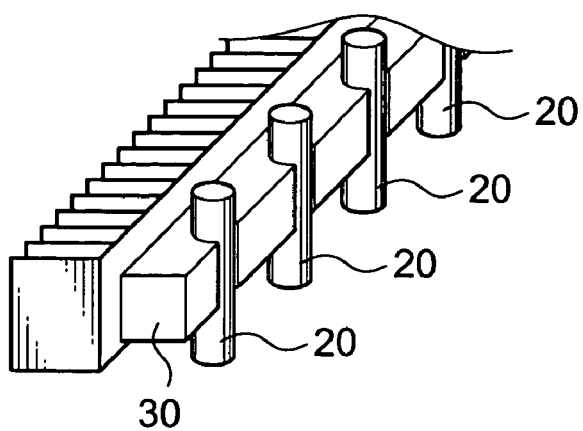
FIG. 18 is a perspective view of the heating block of the microorganism detection apparatus according to the seventh embodiment of the present invention.

As shown in FIG. 18, a heating block 30 in this embodiment is formed so that it can hold the detection target introduction portions 20 of the microorganism detection cassettes 600, and a CCD camera 40 is mounted in the main body 601 so that it is horizontally (transversely) movable above the microorganism detection cassettes 600. During the measurement process at step S8 in FIG. 8 described above, a controller 48 moves the CCD camera 40 to a position immediately above the filter 22 of one of the detection target introduction portions 20, and examines the inside (the filter) of the detection target introduction portion 20 for a color change.

When multiple microorganism detection cassettes 600 can be detached from the main body 601 in this manner, a plurality of examinations can be performed at one time. For example, a sample for which microbial contamination is to be examined can be sealed in the sample syringe of one microorganism detection cassette 600, a sample that has already been contaminated by microorganisms can be sealed in the sample syringe of another microorganism detection cassette 600, and a sample that has not yet been contaminated by microorganisms can be sealed in an additional microorganism detection cassette 600. When the examinations are performed at a time and the results obtained are compared, a determination of microbial contamination can be more precisely performed, and the detection sensitivity can be improved.

Furthermore, since the CCD camera 40 is movably mounted, the optical characteristics of the reagents in multiple detection target introduction portions 20 can be examined by a single CCD camera, so that the costs can be reduced and the detection operation can be more efficiently performed.

As described above in detail, according to the present invention, the microorganism detection apparatus and the microorganism detection cassette can be simplified. Further, the required detection period can be reduced and the detection sensitivity can be improved.

Figure 19:
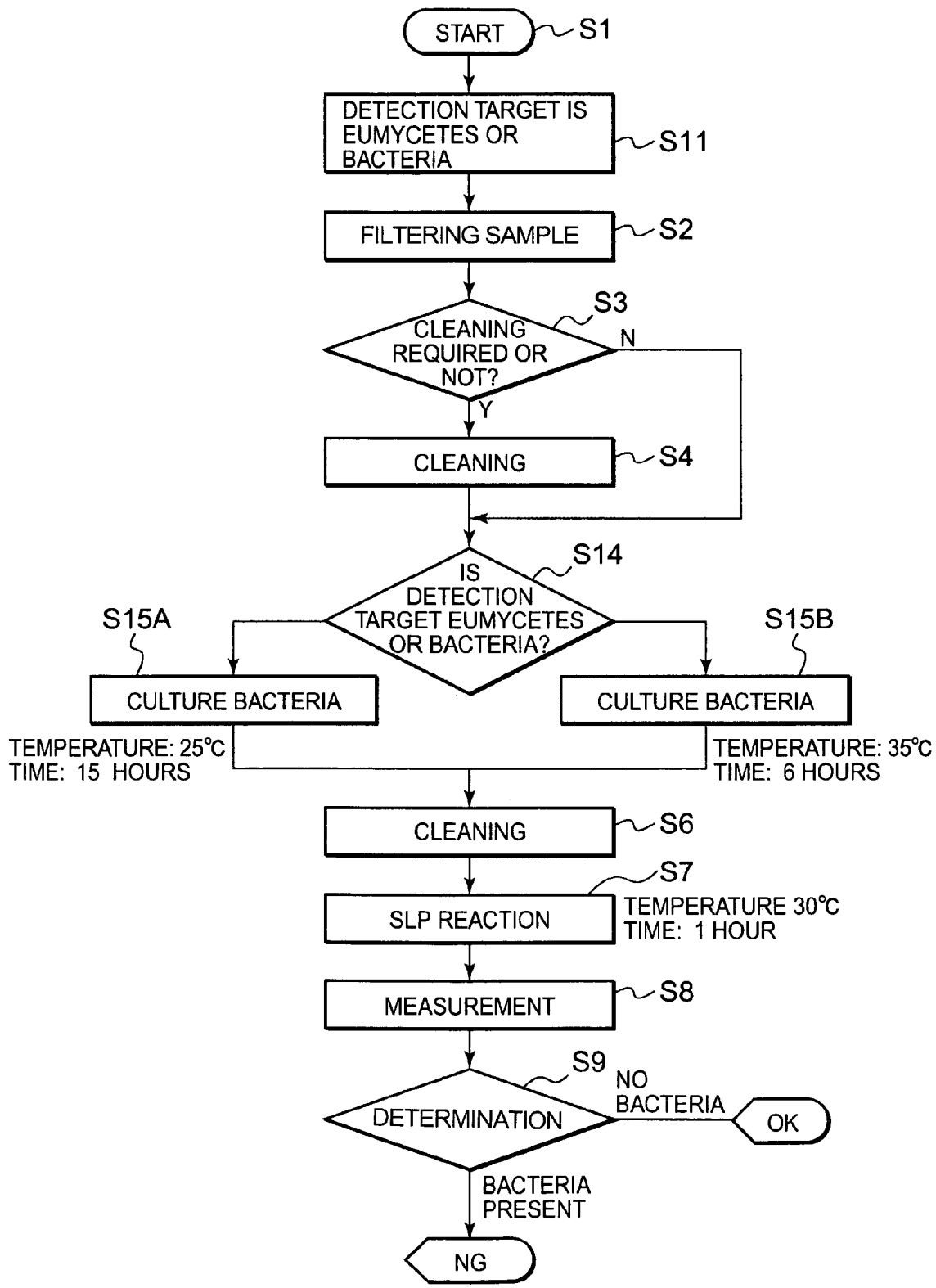
FIG. 19 is a flowchart showing another example of the control process performed by the microorganism detection apparatus.

In the second and the third embodiments, the microorganism detection method has been explained for a case wherein a microorganism to be detected is not specifically identified, and is either an Eumycetes or a bacterium. When a detection target is clearly identified as either an Eumycetes or a bacterium, as shown in FIG. 19, culturing is performed for a period of time and at a temperature that are most appropriate for the pathogen. Since the control operation in FIG. 19 is almost the same as that in FIG. 8, only those processes that differ will be explained.

When the controller 48 is activated at step S1, pathogen information indicating whether a target (sample) is a bacterium or an Eumycetes is input to the controller 48 (step S11 in FIG. 19). A user may directly enter pathogen information into the controller 48, or as described in the third embodiment, identification means, such as a barcode, may be provided for the case, while reading means, such as a barcode reader, for reading the identification means, may be provided for the main body, so that the reading means transmits pathogen information to the controller 48.

When the cleaning at step S4 has been completed, the controller 48 advances to step S14 (when it is determined at step S3 that cleaning is not required, the controller 48 is shifted from step S3 to step S14). Based on the information input at step S11, the controller 48 advances to step S15A when the target is Eumycetes. At step S15A, the controller 48 adjusts to 25° C. the temperature of the interior of the detection target introduction portions 20, and maintains this state for about half a day (e.g., 15 hours). Thus, culturing of the Eumycetes can be performed.

When it is determined at step S14 that the detection target is bacteria, the controller 48 advances to step S15B. At step S15B, the controller 48 adjusts to 35° C. the temperature of the interior of the detection target introduction portions 20, and maintains this state for several hours (e.g., six hours). Since bacteria are propagate more rapidly than do Eumycetes, a microorganism count equaling or exceeding the detection limit of the phenol oxidase precursor can be obtained. In this manner, the culturing of bacteria can be accurately performed, and the examination period can be shortened.

Figure 20:
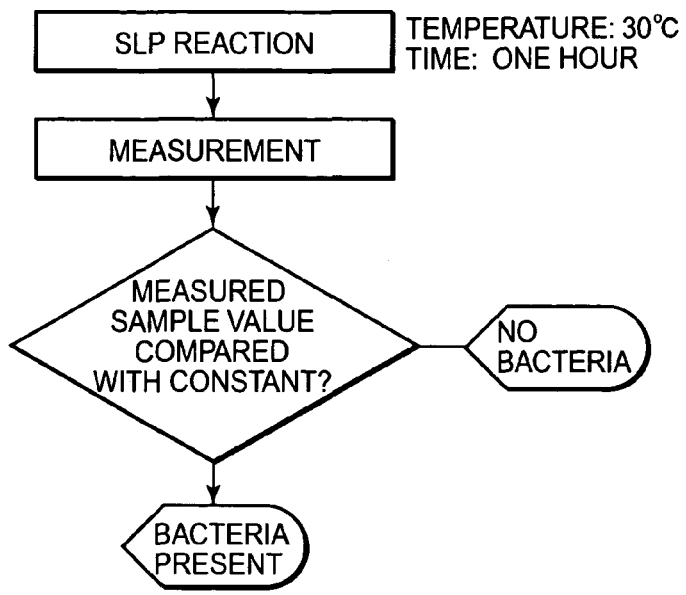
FIG. 20 is a flowchart showing a determination method employed in the determination process for the second to the sixth embodiments.

During the above described determination process, when the controller 48 determines the presence/absence of microorganisms by employing a single sample as in the second to the fifth embodiments, as shown in FIG. 20, predetermined numerical information that indicates a predetermined comparison color tone can be provided in advance for the controller 48. Then, the controller 48 can compare the predetermined numerical information with a numerical value representing the color tone of the sample, and can determine whether microorganisms, such as bacteria or Eumycetes, are present/absent.

Figure 21:
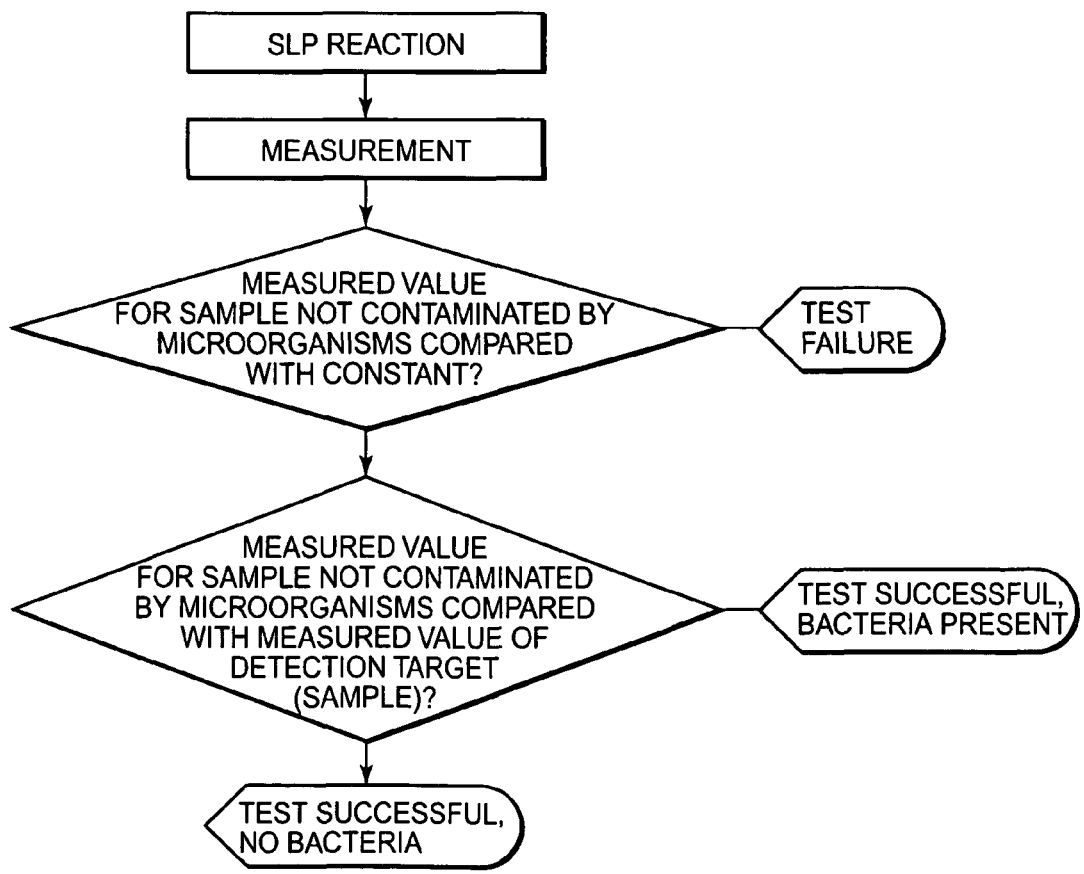
FIG. 21 is a flowchart showing a determination method employed for the determination process of the sixth embodiment.

While referring to FIG. 21, an explanation will now be given for the determination process performed by the controller 48 for a case wherein two examinations are performed at the same time, as in the sixth embodiment, e.g., a case wherein a sample for which microbial contamination has already occurred is sealed in the microorganism detection cassette 500A of the microorganism detection apparatus 510, while a sample that has not yet been contaminated by microorganisms is sealed in the microorganism detection cassette 500B, and the examinations are performed at the same time.

First, numerical value information (hereinafter referred to as a constant) that indicates the color tone of a sample in the microorganism detection cassette 500B and a predetermined color tone that is input in advance, e.g., a color tone that is supposed to exist when no contamination has occurred, is stored in the controller 48. The controller 48 compares a numerical value (hereafter referred to as a measured value) representing a measured color tone with the constant. When the input constant and the measured value of the microorganism detection cassette 500B almost match, the controller 48 compares the measured value for the microorganism detection cassette 500A with the measured value for the microorganism detection cassette 500B. Then, when these values substantially match, the controller 48 determines that microorganisms are not present in the sample in the microorganism detection cassette 500A.

When the measured value for the microorganism detection cassette 500A differs from the measured value for the microorganism detection cassette 500B, the controller 48 determines that microorganisms are present in the sample in the microorganism detection cassette 500A. And when the constant is compared with the measured value for the microorganism detection cassette 500B and there is a great difference between the two, the controller 48 determines that an error occurred during the examination.

Figure 22:
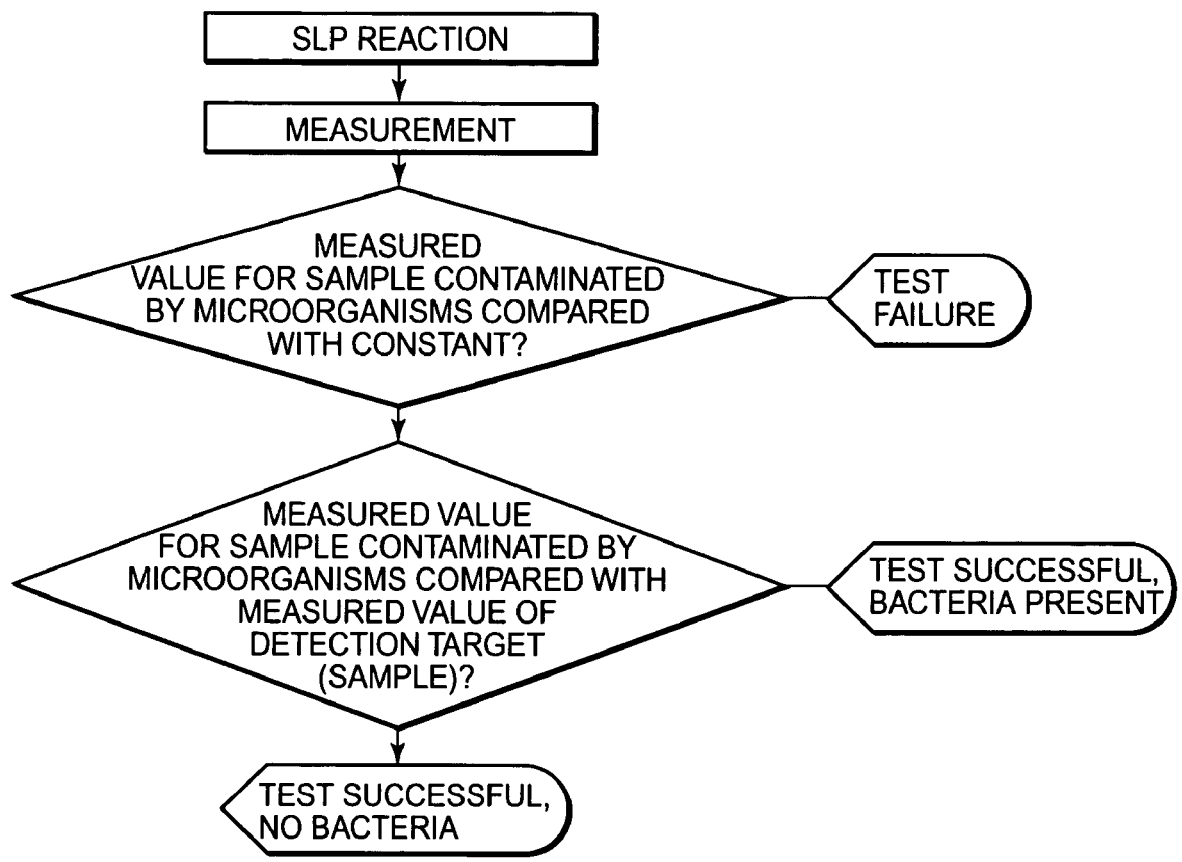
FIG. 22 is a flowchart showing other determination method employed for the determination process of the sixth embodiment.

While referring to FIG. 22, an explanation will now be given for the determination process performed by the controller 48 for a case wherein a sample for which a microbial contamination examination is to be performed is sealed in the microorganism detection cassette 500A of the microorganism detection apparatus 510, while a sample that has already been contaminated by microorganisms is sealed in the microorganism detection cassette 500B, and the examinations are performed at the same time.

First, a measured value for a sample in the microorganism detection cassette 500B and a predetermined constant input in advance, e.g., numerical value information (a constant) that is supposed to be true when microbial contamination has occurred, are stored in the controller 48. The controller 48 compares the constant and the measured value, and when these two substantially match, compares the measured value for the microorganism detection cassette 500A with the measured value for the microorganism detection cassette 500B. When the two measured values substantially match, the controller 48 determines that microorganisms are present in the sample in the microorganism detection cassette 500A.

When the measured value for the microorganism detection cassette 500A differs from the measured value for the microorganism detection cassette 500B, the controller 48 determines that microorganisms are not present in the sample in the microorganism detection cassette 500A. And when the constant and the measured value for the microorganism detection cassette 500B are compared and there is a great difference between the two, the controller 48 determines that an error occurred during this examination.

Figure 23:
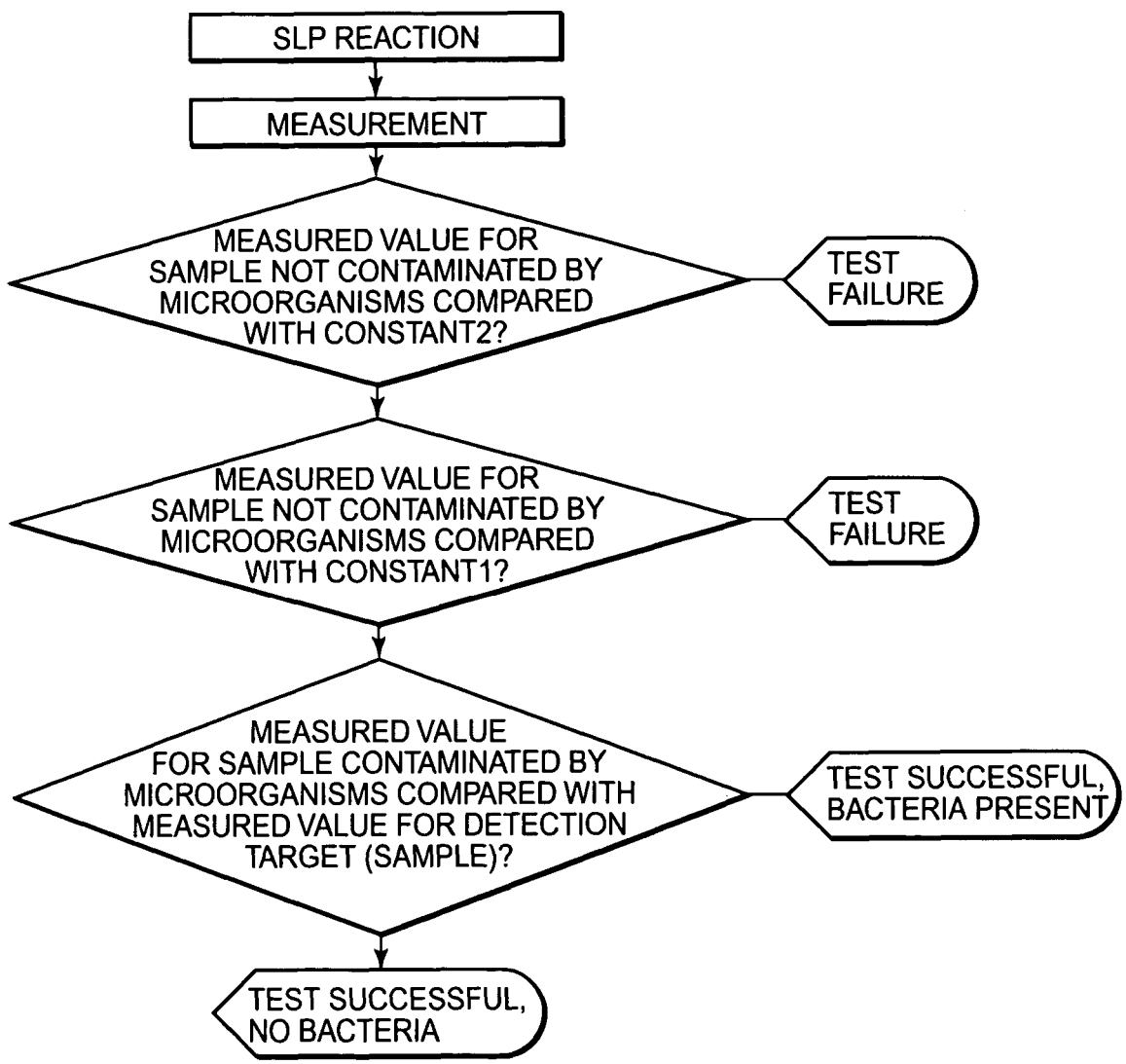
FIG. 23 is a flowchart showing an example determination method employed for the determination process of the seventh embodiment.

While referring to FIG. 23, an explanation will now be given for an example determination process performed by the controller 48 for the seventh embodiment when a plurality of examinations are performed at the same time. In this case, a sample that is to be examined for microbial contamination is sealed in at least one of the microorganism detection cassettes 600 of the microorganism detection apparatus 610, a sample that has not yet been contaminated by microorganisms is sealed in another microorganism detection cassette 600, and a sample that has already been contaminated by microorganisms is sealed in an additional microorganism detection cassette 600.

First, numerical information (a constant 1) that it is estimated is true when microbial contamination has occurred and numerical information (a constant 2) that it is estimated is true when no microbial contamination has occurred are stored in the controller 48. Then, the controller 48 compares measured values with these constants. When the measurement process is completed, the controller 48 compares, with the constant 2, the measured value for the sample that is not contaminated by microorganisms. When these two values substantially match, the controller 48 compares, with the constant 1, the measured value of the sample that is contaminated by microorganisms. When these two values almost match, the controller 48 compares, with the measured value of the sample that is not contaminated by microorganisms, the measured value of the sample for which the microbial contamination examination has been performed. When these measured values substantially match, the controller 48 determines that microorganisms are not present in the sample. When the measured value of the sample that is not contaminated by microorganisms differs from the measured value of the sample for which the microbial contamination examination was performed, the controller 48 determines that microorganisms are present in the sample.

When the measured value for the sample that is not contaminated by microorganisms is different from the constant 2 that has been input in advance, or when the measured value for the sample that is contaminated by microorganisms is different from the constant 1 that has been input in advance, the controller 48 determines that an error occurred during the examination. In this manner, the measured values for multiple samples can be compared to determine whether microorganisms are present/absent, so that a more precise determination can be made.

Figure 24:
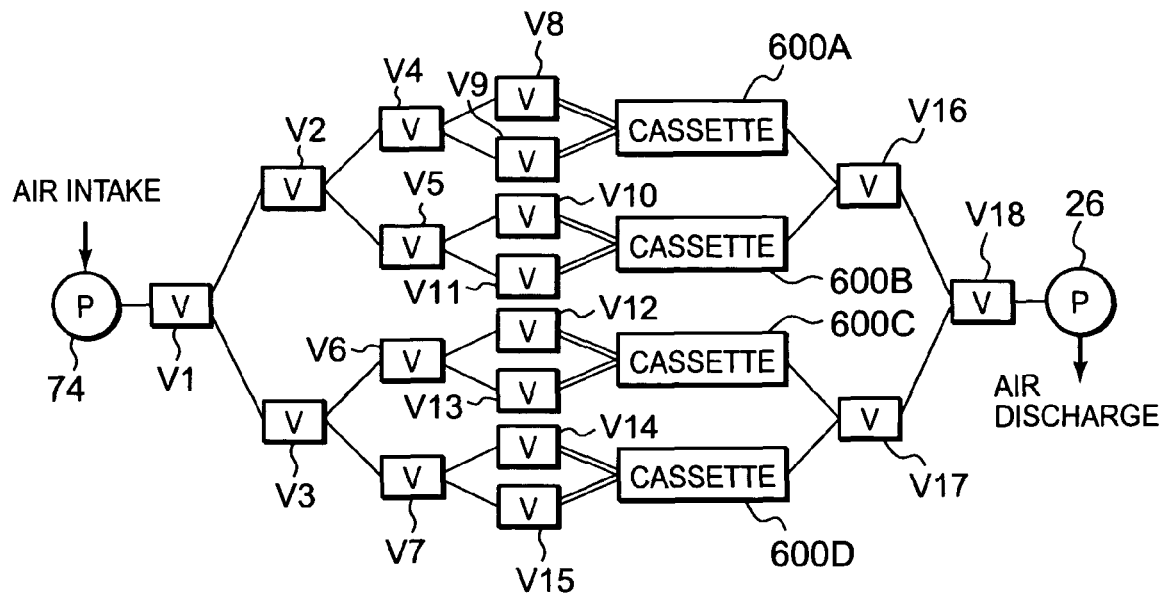
FIG. 24 is a diagram for explaining an example compressed gas supply path for the microorganism detection apparatus of the seventh embodiment.

When a plurality of microorganism detection cassettes 600 are provided as in the seventh embodiment, a single pelister pump can satisfactorily compress gas to be supplied to the individual syringes of the microorganism detection cassettes 600. FIG. 24 is a diagram showing an example in which a single pelister pump is used to supply compressed gas to the individual microorganism detection cassettes 600.

In FIG. 24, solenoid valves V1 to V18 (for example, three-way valves, as well as the solenoid valves 92, 93 and 94 used in the third embodiment) are provided along the individual pipes. A pelister pump 74 is arranged for supplying a compressed gas to syringes (not shown) in the microorganism detection cassettes 600A, 600B, 600C and 600D, and a pelister pump 26 is arranged for transferring, to the liquid waste tank 28, solutions such as samples, culture solutions, washing reagents and detection reagents in the detection target introduction portions 20 of the microorganism detection cassettes 600A, 600B, 600C and 600D.

As shown in FIG. 24, by employing multiple solenoid valves V1 to V18, the supply of gas compressed by one pelister pump 74 can be adjusted for each of the microorganism detection cassettes 600A, 600B, 600C and 600D.

Figure 25:
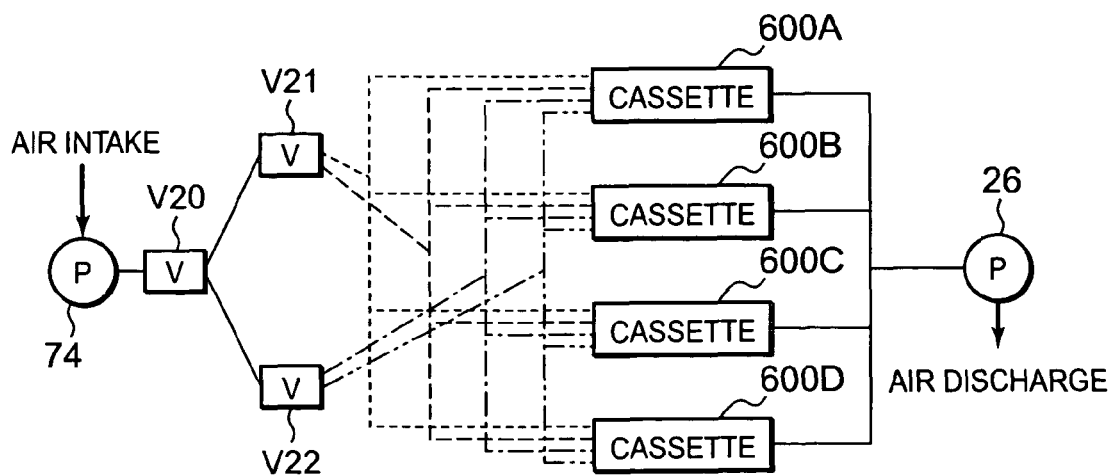
FIG. 25 is a diagram for explaining another example compressed gas supply path for the seventh microorganism detection apparatus of the seventh embodiment.

Further, as shown in FIG. 25, when three solenoid valves V20 to V22 (e.g., three-way solenoid valves, as well as the solenoid valves 92, 93 and 94 used in the third embodiment) are provided along the airpipes, a compressed gas can be supplied to the syringes of all the microorganism detection cassettes 600 at the same time.

For the microorganism detection apparatus and the microorganism detection cassette of each embodiment, it may be preferable that the syringes be cooled or heated to a predetermined temperature in order to prevent the deterioration of a sample, a culture solution and reagents in the syringes during an examination. To cope with this situation, like the detection target introduction portion 20 of each embodiment, the syringes may be held in a heating block on one side of which a Peltier device is provided. With this structure, the heating block need only be cooled or heated by the Peltier device, so that a predetermined temperature can be maintained for the sample, the culture solution and the reagents in the syringes.

An entire microorganism detection apparatus, or an entire microorganism detection cassette may be installed in a space wherein the temperature can be controlled, and the temperature in this space may be managed by using an air conditioner. In this manner, during an examination the deterioration, in the syringes, of a sample, a culture solution and a detection reagent can be prevented.

In the individual embodiments, the reagent sealed in the reagent syringe is a solution, or when a reagent is a solid, the solid is dissolved in a solvent and the liquid is sealed in the reagent syringe. However, it is preferable that a solid reagent be dissolved in a solvent immediately before it is used. Further, when a user must dissolve a solid reagent in a solvent, the process becomes complicated, and germs may enter while the solution is being mixed. Therefore, a holder for a solid reagent, a holder for a solvent used to dissolve the reagent, and a mechanism for mixing the solvent and the reagent immediately before use can also be provided for the microorganism detection apparatus, or the microorganism detection cassette. In this case, a mechanism for dripping the solvent onto the reagent and an appropriate agitating mechanism for vibrating a container wherein the reagent and the solvent are retained must be provided, so that the reagent can be uniformly dissolved in the solvent.

Furthermore, in the individual embodiments, the SLP reagent has been employed, and the CCD camera has detected a color tone change for the filter portion in the detection target introduction portion. However, not only the SLP reagent can be employed for the detection of a color tone change, but also light transmittance or absorbance by the filter portion may be employed for the determination. Further, not only a change in the color tone, but also a change in the hue of the filter portion may be detected.

Further, for a detection process performed for two or more samples while employing a single detector (a measurement unit), in the sixth and seventh embodiments a CCD camera has been provided that is movable relative to the main body. However, instead of arranging the CCD camera so it is movable, a movable microorganism detection cassette may be used. Further, besides a CCD camera, a wide-angle lens may be employed as a detector. In addition, the detector can be located at an arbitrary position, such as above, to the side or below or obliquely positioned relative to the detection filter.

Since for a microorganism detection examination a biochemical reaction is employed, the results obtained during an examination may be changed, depending on the status of various parameters, such as the temperature and humidity. When a mechanism for measuring the temperature and the humidity and a mechanism for recording these parameters are also provided in order to cancel out the affect of parameter fluctuation, the examination accuracy can be improved.

While taking tight sealing into account, the microorganism detection apparatus and the microorganism detection cassette are designed so as to prevent the entry of external microorganisms and to avoid contamination. In preparing for a case wherein the interiors of the microorganism detection apparatus and the microorganism detection cassette are contaminated internally, the apparatus or the cassette should include a mechanism that is formed of a material, or has a structure, that can perform at least one type of sterilization, i.e., UV pasteurization, ozone exposure, hydrogen peroxide exposure, high-temperature high-pressure pasteurization or water cleaning. Or, as another example, an apparatus may be constituted by units, and only a unit that is contaminated is removed and cleaned by a mechanism that can perform sterilization or can remove contamination using one of the above methods.

Furthermore, in order to prevent contamination in the detection target introduction portion due to an overflow of a sample, a culture solution, a washing reagent or a detection reagent that is fed into the detection target introduction portion, a mechanism for monitoring and preventing overflow may be provided for the filter. Then, when it is apparent an overflow could occur, the controller could halt the feeding of the liquid into the detection target introduction portion.

Since the microorganism detection cassette is a precision instrument, the setting of the cassette, the occurrence of line disconnection, and apparatus defects due to the failure of a pump or a valve should be checked for before an examination. Therefore, when the microorganism detection apparatus includes a mechanism (a self-check) for performing these checks before an examination, and a mechanism for storing the results, a user need only read the self-check record to easily determine the condition of the apparatus.

In addition to the above described embodiments, a mechanism (a microorganism detection apparatus) having the same functions as each embodiment can also be provided using a distribution robot.

The present invention relates to a general-purpose microorganism detection apparatus that is highly sensitive and can detect microorganisms quickly, not only in a culture solution used for cell culturing, but also in foods and liquids such as liquors, non-alcoholic beverages and fruit juices and water used for cleaning during food processing, in the air (at filters through which air passes) in a hygienically maintained environment, or in all other fluids (liquids or gases), such as the water used for cleaning semiconductors, for which microorganism detection is desired.

What is claimed is:

1. A microorganism detection apparatus comprising:
a detection target introduction portion, into which a sample and reagents are to be introduced, wherein said detection target introduction portion is disposable;
a detector, for detecting optical characteristics of the reagent introduced into the detection target introduction portion, wherein said detector detects color tone of the reagent introduced into the detection target introduction portion;
a light source;
a sample holder, for holding the sample to be introduced into the detection target introduction portion;
a culture solution holder, for holding a culture solution used to culture a microorganism;
reagent holders, for holding the reagents to be introduced into the detection target introduction portion, wherein the presence/absence of microorganisms in the sample is determined in accordance with optical characteristics detected by the detector;
a temperature controller, located near the detection target introduction portion, for controlling temperature at the detection target introduction portion;
a waste liquid collection portion, provided for collecting waste liquid for the sample, the culture solution or the reagents discharged from the detection target introduction portion; and
a pressurizing unit, for pressurizing the sample holder, the culture solution holder and the reagent holders,
wherein:
the detector detects a color tone or absorbance of the reagent, and the presence/absence of microorganisms in the sample is determined in accordance with the color tone or the absorbance of the reagent detected by the detector,
the culture solution is introduced into the detection target introduction portion and is used to culture the microorganisms in the detection target introduction portion,
the sample holder, the culture solution holder and the reagent holders are integrally formed,
a holder mounting unit is provided that is detachable from said microorganism detection apparatus,
the pressurizing unit includes a gas compression unit,
the pressurizing unit feeds the sample in the sample holder, the culture solution in the culture solution holder and the reagents in the reagent holders directly to the detection target introduction portion, and
the sample holder, the culture solution holder and the reagent holders have volumes of the sample, culture solution and reagents, respectively, so that when the pressurizing unit pressurizes each of the sample holder, the culture solution holder and the reagent holders, all of the sample, the culture solution and the reagents in the sample holder, the culture solution holder and the reagent holders, respectively, is expelled from each holder through a single pressurization.

2. A microorganism detection apparatus according to claim 1, further comprising:
a plurality of sets of sample holders, culture solution holders, reagent holders, detection target introduction portions, and waste liquid collection portions, for collecting waste liquid for the sample, the culture solution or the reagents discharged from the detection target introduction portions.

3. A microorganism detection apparatus according to claim 2, wherein the optical characteristics of the reagent introduced into the plurality of detection target introduction portions are detected by employing a single detector.

4. A microorganism detection apparatus according to claim 1, wherein the culture solution holder, the reagent holders and the detection target introduction portion are mounted together in a single case that is tightly closed; and wherein a communication portion, used to supply a compressed gas from the gas compression unit to the culture solution holder and the reagent holders, is provided in the case.

5. A microorganism detection apparatus according to claim 4, wherein the sample holder is integrally formed in the case and a communication portion, used to supply a compressed gas from the gas compression unit to the sample holder, is provided in the case.

6. A microorganism detection apparatus according to claim 4, wherein the sample holder is connectable to the case.

7. A microorganism detection apparatus according to claim 4, wherein the waste liquid collection portion, for collecting the waste liquid for the sample, the culture solution or the reagents discharged from the detection target introduction portion, is integrally formed with the case.

8. A microorganism detection apparatus according to claim 4, wherein the waste liquid collection portion, for collecting the waste liquid for the sample, the culture solution or the reagents discharged form the detection target introduction portion, is connectable to the case.

9. A microorganism detection apparatus according to claim 2, wherein a different case is provided for each detection target introduction portion, and an identification unit for identifying the detection target introduction portion in accordance with the case is provided.

10. A microorganism detection cassette,
wherein a detection target introduction portion, into which a sample and a reagent are to be introduced, a culture solution holder for holding a culture solution to be introduced to the detection target introduction portion for culturing a microorganism, and reagent holders for holding the reagents to be introduced to the detection target introduction portion, are mounted together in a single case;
wherein a communication portion is provided for the case and is used to supply a compressed gas to each of the culture solution holder and the reagent holders;
wherein the culture solution holder and the reagent holders have volumes of the culture solution and reagent, respectively, so that when the communication portion supplies compressed gas to each of the culture solution holder and reagent holders, all of the culture solution and the reagents in the culture solution holder and the reagent holders, respectively, is expelled from each holder through a single application of the compressed gas, and
wherein said detection portion detects color tone of the reagent introduced into the detection target introduction portion.

11. A microorganism detection cassette according to claim 10,
wherein a sample holder, for holding a sample to be introduced into the detection target introduction portion, is mounted together in the case, and a communication portion, for supplying the compressed gas to the sample holder, is provided for the case, and
wherein the sample has a volume such that all of the sample is expelled from the sample holder during a single application of the compressed gas.

12. A microorganism detection cassette according to claim 10,
wherein a sample holder, for holding a sample to be introduced into the detection target introduction portion by the compressed gas, is connectable to the case, and
wherein a volume of the sample in the sample holder is configured such that all of the sample is expelled from the sample holder during a single application of the compressed gas.

13. A microorganism detection cassette according to one of claims 10 to 12, wherein a waste liquid collection portion, for collecting the waste liquid for the sample, the culture solution or the reagents discharged from the detection target introduction portion, is integrally formed with the case.

14. A microorganism detection cassette according to one of claims 10 to 12, wherein a waste liquid collection portion, for collecting the waste liquid for the sample, the culture solution or the reagents discharged form the detection target introduction portion, is connectable to the case.

* * * * *